(12) United States Patent
Chizeck et al.

(10) Patent No.: US 9,686,306 B2
(45) Date of Patent: Jun. 20, 2017

(54) USING SUPPLEMENTAL ENCRYPTED SIGNALS TO MITIGATE MAN-IN-THE-MIDDLE ATTACKS ON TELEOPERATED SYSTEMS

(71) Applicant: UNIVERSITY OF WASHINGTON THROUGH ITS CENTER FOR COMMERCIALIZATION, Seattle, WA (US)

(72) Inventors: Howard Jay Chizeck, Seattle, WA (US); Tamara Bonaci, Seattle, WA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 0 days.

(21) Appl. No.: 14/438,722

(22) PCT Filed: Oct. 30, 2013

(86) PCT No.: PCT/US2013/067528
§ 371 (c)(1),
(2) Date: Apr. 27, 2015

(87) PCT Pub. No.: WO2014/116314
PCT Pub. Date: Jul. 31, 2014

(65) Prior Publication Data
US 2015/0295949 A1    Oct. 15, 2015

Related U.S. Application Data

(60) Provisional application No. 61/721,936, filed on Nov. 2, 2012.

(51) Int. Cl.
*H04L 29/06* (2006.01)
*H04L 12/12* (2006.01)
(Continued)

(52) U.S. Cl.
CPC ...... *H04L 63/1441* (2013.01); *G06F 19/3418* (2013.01); *G06F 19/3481* (2013.01);
(Continued)

(58) Field of Classification Search
CPC ......... G06F 9/54; G06F 17/3089; H04N 7/12; H04N 19/34; H04N 19/30; H04N 19/61;
(Continued)

(56) References Cited

U.S. PATENT DOCUMENTS 6,493,587 B1    12/2002  Eckmiller et al.
7,162,665 B2 *   1/2007  Masuda ............... G06F 11/0727
                                                    702/183
(Continued)

FOREIGN PATENT DOCUMENTS

WO    2010/141375 A2    12/2010
WO    2012/015543 A2     2/2012

OTHER PUBLICATIONS

Bonaci, et al., "On Potential Security Threats Against Rescue Robotic Systems," 2012 IEEE International Symposium on Safety, Security, and Rescue Robotics (SSRR), pp. 1-2, 2012.
(Continued)

Primary Examiner — Thanhnga B Truong
(74) Attorney, Agent, or Firm — McDonnell Boehnen Hulbert & Berghoff LLP

(57) ABSTRACT

Methods and systems for securing remotely-operable devices are provided. A remotely-operable device can receive a command related to a component of the remotely-operable device operating in an environment. The remotely-operable device can include a reality-rules database (RRDB) that is configured to store a plurality of reality rules with each reality rule relating to a constraint on the remotely-operable device. The remotely-operable device can determine a reasonableness value for the command based on a
(Continued)

constraint, where the constraint is determined based on a constraint related to at least one reality rule of the plurality of reality rules stored in the RRDB. The remotely-operable device can encode the reasonableness value for the command in a feedback message. The remotely-operable device can send the encoded feedback message from the remotely-operable device.

21 Claims, 10 Drawing Sheets

(51) Int. Cl.
    *G06F 19/00*     (2011.01)
    *A61B 34/30*     (2016.01)

(52) U.S. Cl.
    CPC .......... *H04L 12/12* (2013.01); *H04L 63/1416* (2013.01); *A61B 34/30* (2016.02)

(58) Field of Classification Search
    CPC ......... H04N 19/70; H04L 12/24; H04L 29/06; H04L 29/08; H04L 1/0061; H04L 1/1671; H04W 4/00; G06Q 30/02; G06Q 10/10
    USPC .......... 726/23; 719/313; 715/760; 375/240.7; 370/329
    See application file for complete search history.

(56) References Cited

U.S. PATENT DOCUMENTS

| | | | |
|---|---|---|---|
| 8,195,333 B2 | 6/2012 | Ziegler | |
| 8,275,051 B2* | 9/2012 | Hannuksela | .......... H04L 1/0061 370/329 |
| 8,485,085 B2 | 7/2013 | Goree et al. | |
| 2002/0075307 A1* | 6/2002 | Alexander | .............. H04L 29/06 715/760 |
| 2003/0060808 A1 | 3/2003 | Wilk | |
| 2005/0108484 A1* | 5/2005 | Park | .................... G06F 11/1448 711/162 |
| 2008/0313356 A1* | 12/2008 | Blinn | ...................... H04L 51/04 710/7 |
| 2009/0036750 A1 | 2/2009 | Weinstein et al. | |
| 2009/0311963 A1 | 12/2009 | Haverty | |
| 2011/0041160 A1 | 2/2011 | Choi | |
| 2011/0302414 A1 | 12/2011 | Logan et al. | |
| 2012/0239060 A1 | 9/2012 | Orban, III | |
| 2014/0068770 A1 | 3/2014 | Chizeck et al. | |

OTHER PUBLICATIONS

Burian, et al., "Building Safe Realtime Channel for Mobile Teleoperated Robots," Annals of Daaam for 2010 and Proceedings of the 21st International DAAAM Symposium, Zadar, Croatia, ISSN: 1726-9679, ISBN: 978-3-901509-73-5, B. Katalinic (Ed.), DAAAM International Vienna: Vienna, pp. 1209-1210, 2010.
Gage, et al., "ShadowBowl 2003: Lessons Learned from a Reachback Exercise with Rescue Robots," IEEE Robotics and Automation Magazine, pp. 62-69, 2004.
King, et al., "Preliminary protocol for interoperable telesurgery," IEEE International Conference on Advanced Robotics, pp. 1-6, 2009, 2009.
Li, "Web-based Remote Monitoring and Control for Process Plants," Proceedings of the 2005 International Conference on Machine Learning and Cybernetics, vol. 2, pp. 936-941, 2005.
Lum, et al., "Field operation of a surgical robot via airborne wireless radio link," Proceedings of the IEEE International Conference on Field and Service Robotics, pp. 1-7, 2007.
Murphy, "CRASAR in Japan! Fukushima, recovery operations update," available online at: http:/crasar.org/blog/page/6/, 2011.
Murphy, "Human-robot interaction in rescue robotics," IEEE Transactions on Systems, Man, and Cybernetics, Part C: Applications and Reviews, vol. 34, No. 2, pp. 138-153, 2004.
Murphy, "The 100:100 challenge for computing in rescue robotics," 2011 IEEE International Symposium on Safety, Security, and Rescue Robotics, pp. 72-75, 2011.
Pang, et al., "Secure Transmission Mechanism for Networked Control Systems under Deception Attacks," IEEE.
PCT/US2013/067528 (filed Oct. 30, 2013), International Search Report and Written Opinion dated Aug. 20, 2014.
Pianigiani, et al., "Italian Crews Struggle to Secure Cruise Ship," The New York Times, available online at: http://www.nytimes.com/2012/01/21/world/europe/costa-concordia-cruise-ship-operations-suspended-again.html?_r=0, 2012.
Serpanos, et al., "Defense against man-in-the-middle attack in client-server systems," Sixth IEEE Symposium on computers and Communications, pp. 9-14, 2001.
Tanaka, et al., "A Tricycle-style Teleoperational Interface that Remotely Controls a Robot for Classroom Children," 7th ACM/IEEE International Conference on Human-Robot Interaction (HRI), pp. 255-256, 2012.
Yang,: "Safety and Security Checking," Internet-based Control Systems: Design and Applications, Chapter 10, pp. 131-145, 2011.

* cited by examiner

USING SUPPLEMENTAL ENCRYPTED SIGNALS TO MITIGATE MAN-IN-THE-MIDDLE ATTACKS ON TELEOPERATED SYSTEMS

CROSS-REFERENCE TO RELATED APPLICATIONS

This application is a U.S. national phase of International Application No. PCT/US2013/067528, filed on Oct. 30, 2013, which claims priority to U.S. Provisional Application No. 61/721,936, filed Nov. 2, 2012, both of which are incorporated by reference herein in their entirety.

STATEMENT OF GOVERNMENT RIGHTS

This invention was made with government support under Grant No. 0930930, awarded by the National Science Foundation (NSF). The government has certain rights in the invention.

BACKGROUND OF THE INVENTION

Unless otherwise indicated herein, the materials described in this section are not prior art to the claims in this application and are not admitted to be prior art by inclusion in this section.

Advances in robotics, embedded and information systems are enabling a rapid development of teleoperated robotic systems. In telerobotic applications such as bomb disposal, remotely operated aircraft and underwater vehicles, search and rescue and robotic surgery, robots primarily serve as extensions of people. Human operators, often geographically distant, interact with robots through a communication channel.

Natural and human-caused disaster circumstances impose specific constraints on teleoperated robotic systems. The systems are expected to operate with limited power resources, often lacking a basic infrastructure, and in challenging climates and environments. Some of the applications of such systems include handling radioactive material; operating unmanned vehicles for air (e.g., UAV, drone), space (e.g., near Earth's orbit or a manned platform or vehicle), land, and underwater (e.g., ROV) exploration; and telesurgery. With an increase in possible applications, however, the risk of such systems being misused, deliberately tampered with, or even compromised increases as well. These security threats are especially harmful if teleoperated robotic systems are used for inspection, repair and manipulation, such as in telerobotic surgery systems.

In some embodiments, secure processors are utilized. Secure coprocessors can include dedicated chips, microprocessors or computers, which provide tamper-resistance and enable executing of cryptographic method. Various applications of secure coprocessors have been proposed for use in commercial, military, and electronic voting applications.

SUMMARY

In one aspect, a method is provided. A remotely-operable device receives a command related to a component of the remotely-operable device operating in an environment. The remotely-operable device includes the component and a reality-rules database (RRDB). The RRDB is configured to store a plurality of reality rules, where each reality rule relates to a constraint on the remotely-operable device. The remotely-operable device determines a reasonableness value for the command based on at least one constraint on the remotely-operable device, where at least one constraint is determined based on at least one constraint related to at least one reality rule of the plurality of reality rules stored in the RRDB of the remotely-operable device. The reasonableness value for the command is encoded in a feedback message for the remotely-operable device. The encoded feedback message is sent from the remotely-operable device.

In another aspect, a method is provided. An operator device determines a first command for a remotely-operable device. The operator device determines a future status of the remotely-operable device and a backup command of the remotely-operable device. The future status includes a predicted status after an associated command is at least partially executed by the remotely-operable device. The backup command is configured to be carried out by the remotely-operable device after the remotely-operable device determines that the associated command is not feasible for at least partial execution. The operator device generates a command message that includes the first command, the future status, and the backup command. The operator device sends the command message.

In another aspect, a remotely-operable device is provided. The remotely-operable device includes a component, a processor and a non-transitory tangible computer readable medium. The non-transitory tangible computer readable medium is configured to store at least a RRDB and executable instructions. The RRDB is configured to store a plurality of reality rules, where each reality rule relates to a constraint on the remotely-operable device. The executable instructions, when executed by the processor, cause the remotely-operable device to perform functions. The functions include: receiving a command related to the component operating in an environment; determining a reasonableness value for the command based on at least one constraint on the remotely-operable device, where at least one constraint is determined based on at least one constraint related to at least one reality rule of the plurality of reality rules stored in the RRDB; encoding the reasonableness value for the command in a feedback message; and sending the encoded feedback message.

DETAILED DESCRIPTION

Figure 1A:
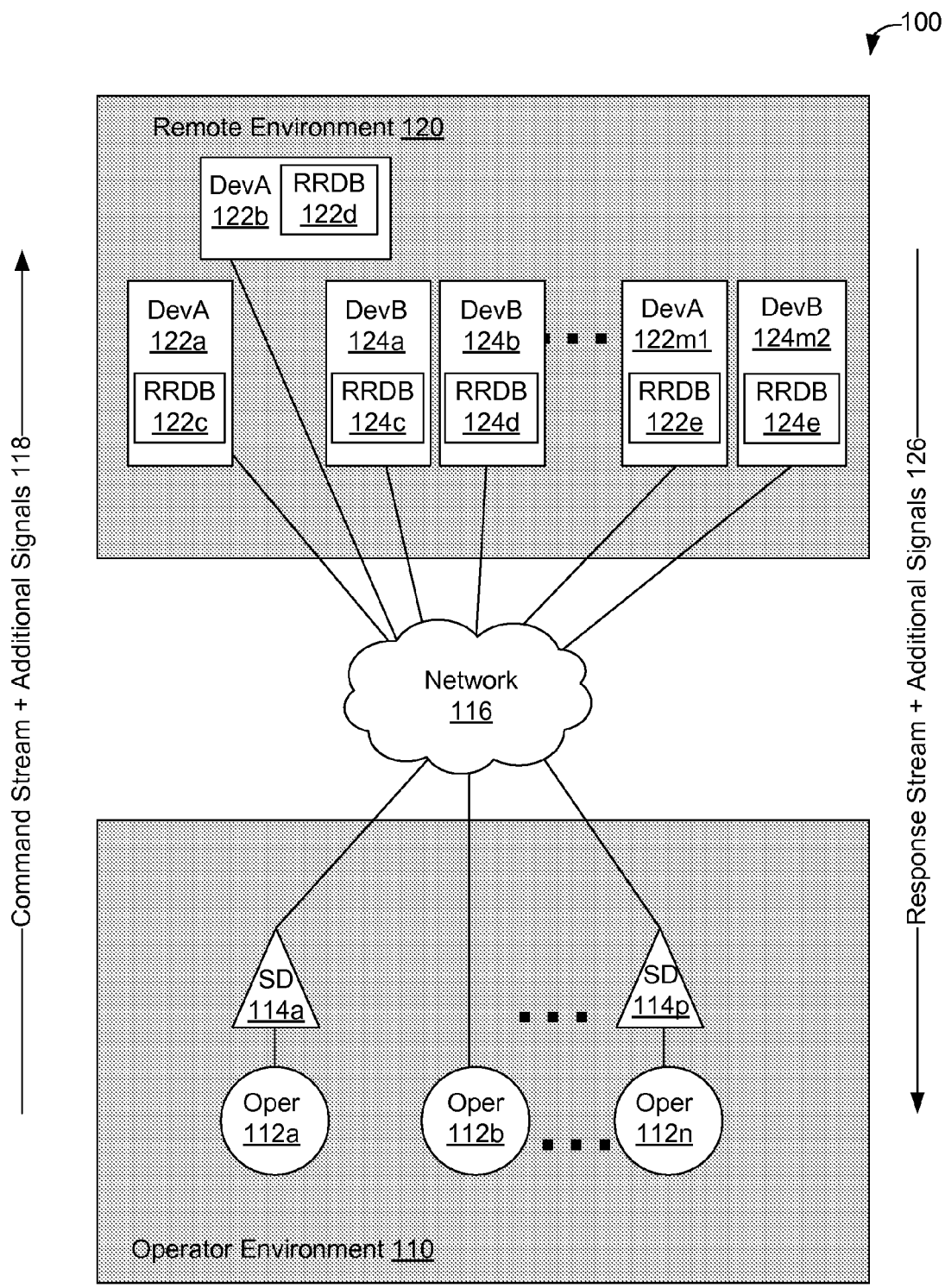
FIGS. 1A, 1B, 1C, and 1D each illustrate an example operating environment for remotely-operable devices, in accordance with an embodiment.

In teleoperated systems, one or more operators can control one or more remotely-operable devices through a communication network. For example, in telerobotic surgery systems, one or more distant surgeons control surgical and other medical manipulator(s) through a communication network. Then, surgical procedures can be viewed as an information exchange between a surgeon and a surgical manipulator and the telerobotic surgery system can be seen as an information system.

A communication network consisting of several wired and wireless components can enable communication for the telerobotic surgical system. In 2007, a telerobotic surgical manipulator ("Raven") was deployed in the Mojave Desert and remotely operated from long distance, using a combination of wired internet and wireless communication (the last segment involving wireless communication with a UAV (unmanned aerial vehicle) circling overhead. Several field experiments were conducted. During this experiment, the following network stochastic conditions were observed: increased communication latency, increased jitter, and additional packet losses, delays, and out-of-order-arrivals.

In addition to stochastic, but benign network patterns, surgeon-manipulator communication over publicly available, or even dedicated wireless networks exposes telerobotic surgery systems to novel set of problem which were not present in hospital settings. For example, the relatively open and uncontrollable nature of communication networks renders telerobotic surgery systems susceptible to attacks mounted by malicious entities adversaries). As an example, consider the following telerobotic surgery system: a surgeon controls a remote surgical manipulator deployed in a desert-like, military environment, where the communication network between the surgeon and the manipulator consists of multiple wired and wireless components. An adversary can attempt to jam, disrupt or even take over the communication network between the surgeon and the manipulator, with the intent to harm wounded soldiers and increase human casualties.

Malicious attacks against telerobotic systems, such as telerobotic surgery systems, can be classified into the following five groups: (1) attacks against wireless communication, (2) attacks on the Internet-enabled surgeon-manipulator interaction, (3) attacks on the surgeon-side software, (4) attacks on the manipulator-side software, and (5) physical attacks. Each attack against a telerobotic system can affect both the manipulator and the human operators; e.g., surgeons or other medical personnel in the case of telerobotic surgery systems.

The message exchange between a surgeon and a manipulator in telerobotic surgical systems can be defined using the Interoperable Telesurgery Protocol (ITP). In the ITP, messages are exchanged using the User Datagram Protocol (UDP). UDP is a minimal-latency transport layer protocol, but does not provide a reliable service. Commanded surgical tool motions are, however, made in very small increments, so possible negative effects of the UDP's unreliability can be reduced by transmitting a surgeon's inputs in small increments. In ITP, control messages, force feedback messages, and video feedback messages are unencrypted and unauthenticated. That is, upon receiving the control message, the manipulator cannot verify that it was the surgeon who sent the message.

An adversary within a remotely-operable device's communication range can misuse and disrupt this unencrypted ITP communication channel using different attacks. In an eavesdropping attack, an adversary can passively listen to the communication between one or more surgeon(s) and the remotely-operable device(s). In a jamming attack, the adversary can deliberately introduce noise into a communication channel to increase the communication delay between the surgeon and the remotely-operable device. In some cases, jamming can completely disrupt message exchange and effectively disable the surgical telerobotic system. In a message modification/false data injection attack, the adversary can modify transmitted messages and/or inject false messages to destabilize the remotely-operable device. By spoofing surgeon control inputs, the adversary may cause the remotely-operable device to move in an undesired and unsafe direction.

For example, consider a jamming attack against a surgical manipulator; e.g., the Raven surgical manipulator mentioned above, where the surgical manipulator enters an emergency state if surgical manipulator does not move within a specified time; e.g., 500 milliseconds (ms). First, the surgeon can send a valid control command to the surgical manipulator. The surgical manipulator can receive and perform the valid control command and send a force feedback message to the surgeon. The surgeon, upon receiving the force feedback, can generate a second control message and send the second control message to the surgical manipulator. The second message is, however, corrupted by a jamming signal, and so the surgical manipulator cannot carry out the second control message. Later, a new incremental movement message is sent to the surgical manipulator, but this message is again corrupted by the jamming signal. Since all received messages are corrupted by the jamming signal, the surgical manipulator is unable to move for more than 500 ms, and so enters an emergency state.

Additionally, lack of authentication between a surgeon and a surgical manipulator can leave surgical teleoperation sessions vulnerable to man-in-the-middle (MITM) attacks, where an adversary: (1) blocks valid messages between a surgeon and a manipulator and (2) creates independent connections with both entities. With a successful MITM attack, the adversary gains control over the procedure, while making the surgeon and the manipulator believe they are talking to each other. As such, MITM attacks are especially malicious, since the adversary may exploit different properties of telerobotic surgery systems to mount them. Moreover, the MITM adversary becomes a part of the system, and can completely compromise the system.

In order of increasing level of impact, the following types of the MITM attack are possible: (1) a delay attack, where the adversary delays received messages for some chosen amount of time before forwarding them to the intended recipient, (2) a replay attack, where an adversary receives messages and replays them to the recipient, (3) message dropping attack, where the adversary simply drops some or all of the received messages, (4) combined delay and message dropping attacks, where the adversary randomly delays some, and drops other messages, possibly in both directions, and (5) message modification/spoofing attacks, where an adversary modifies received messages, and/or creates "spoofed" or false messages in order to render the procedure unsafe.

For example, consider a message spoofing MITM attack where the adversary allows transmission of control messages, but spoofs feedback messages. In this attack, the adversary can receive a control message from the surgeon, and forward the control message to the Raven. The Raven carries out the control message and generates a force feedback message in response that informs the surgeon of its current position. The adversary can then block the valid feedback message and instead send a spoofed feedback message to the surgeon with an incorrect location. The surgeon accepts the spoofed message as valid and commands a new move to change the Raven's current position as indicated in the spoofed feedback message. The adversary forwards the control message with the new move, which is then carried out by the Raven. The adversary again blocks the valid force feedback message, and instead sends another spoofed feedback message to the surgeon, with another incorrect location. Then, the surgeon again commands another move to the manipulator to correct the manipulator's current position, which is specified as incorrect in the feedback message. At this point, after implementing the received message, the Raven may exit an allowed operating area, and enter into an invalid, or even harmful, area of an operating environment.

In order to have patient-safe telerobotic surgical systems, in other words, systems where a patient's well-being and safety can be established, maintained and guaranteed through the whole procedure, despite harsh operating conditions and hostile environments, teleoperated surgery systems need security. It has been argued by many security experts that complex systems are secured best when security solutions are incorporated in the system design from the start.

A security system for telerobotic operation can include a monitoring system, e.g., acting as an intrusion detection and prevention (IDP) system, and an error detection system. The monitoring system can collect information from the operators and the remotely-operable device, as well as about their interactions and communications, to detect both malicious intrusions into the system and benign random failures of the remotely-operable device or the network. Example benign failures and malicious intrusions include (a) malfunctions of the remotely-operable device; (b) reduced remotely-operable device responsiveness due to a failure, (c) benign network issues (such as latency), (d) reduced remotely-operable device and/or network responsiveness due to an attack and (e) spoofed adversarial attempts to disrupt a teleoperated procedure.

In some embodiments, the monitoring system can perform a real-time identification of the unique operator's movement features based on the collected data. That is, the monitoring system can recognize the operator's movement signature. A timely and reliable detection of any discrepancy between an authorized and a spoofed operator (or a disabled operator having erroneous movements) will enable quick detection of adversarial activities, as well as possible anomalies in telerobotic procedures or operator impairment.

The error detection system can use knowledge of physical constraints of a cyber-physical system at the operator side, as well as the remote location. Error detection can reduce uncertainties about the system and can therefore be used in securing the system. The error detection system can add the above-mentioned additional signals encoded as (pseudo) random signals to a body of an unencrypted control message or unencrypted feedback message.

The additional signals can convey device data about a device and/or message control information regarding the interpretation of additional signals, control messages, and/or feedback messages for a device. Additional signals can convey the device data about one or more devices, such as, but not limited to, a remotely-controllable device, an operator device, and/or a security device. Device data conveyed in additional signals, can include, but is not limited to, data about a status, mode, and/or other aspects of a device, data about a message sent or received by the device, sensor data related to the device, and combinations thereof.

The message control information can control interpretation of messages and signals conveyed between remotely-operable device(s), operator device(s), security device(s) and/or other device(s). The message control information can include, but is not limited to, information regarding association of messages and additional signals (e.g., interpret additional signals received in message numbered N with regards to a body of message numbered N+m or N−m with N≥m≥0), information indicating that some or all of the additional signals encoded with one or more designated messages are to be considered as (in)valid, information indicating that part or all of the bodies of one or more designated messages are to be considered as (in)valid, and combinations thereof.

The error detection system can use the additional signals to: (i) verify the content and the freshness of exchanged messages; (ii) recover content of possibly corrupted data; and (iii) in the case of longer delays or denial-of-service attacks, possibly enable a remote remotely-operable device to switch to an autonomous operating mode.

One approach for error detection is to use state estimators, such as Kalman Filters, Extended Kalman Filters, or Unscented Kalman Filters for nonlinear models, as part of a system for matching a time-series shape of an observed process to various known failures in the observed process. Using a recursive maximum likelihood approach, the probability of different known failure modes can be determined in real time; if the observed process shows an unusual and/or unknown failure, then the observed process can be classified as likely being subject to an attack. Once classified as under attack, the system can generate alerts about the attack and/or initiate contingency operation of the system (such as safe shutdown procedures).

In the context of telerobotic surgical systems, and other real-time robotic control systems, time can be of the essence. Specifically, telerobotic surgery systems may have to limit communication delays, including any security overhead, in both directions to 500 ms or less.

One technique to provide rapid monitoring and error detection of telerobotic systems is to monitor and detect errors using additional signals that enable verification the content of received messages, and predict a possible range of future messages. Taken together, the monitoring and error detection systems can enhance the security of telerobotic systems, such as systems that include the Raven surgical manipulator, a mobile grasping robot, and other remotely operated robotic devices.

The additional signals can be based on constraints arising from the interaction of remotely-operable devices with the physical environment to provide additional information about the structure of the system. The information about the structure of the system can be stored in a "reality rules data base" (RRDB) resident on each remotely-operable device. Each reality rule can be related to a constraint on part or the entire remotely-operable device; e.g., a rule related to a range of motion of an actuator, a rule related to movement while in a particular region of an operating environment. The RRDB is not transmitted during remotely-operable device operation; rather, existence of the RRDB is kept secret. Upon receipt of a command, the remotely-operable device can extract information from the command related to the physical environment and/or the structure of the remotely-operable device system.

The remotely-operable device can use the extracted information to query the RRDB and determine whether the command is reasonable based on the physical environment and the structure of the remotely-operable device system. For example, suppose a reality rule in the RRDB specified that a component C of the remotely-operable device had a range of motion of (−90°, +90°) in a dimension D, and the component had a D dimension position at +60°. Then, upon receipt of a first command to move C by +20° in dimension D, the remotely-operable device could extract the information about C from the first command and query the RRDB with the current position of C and extracted information. Then, the RRDB can determine that the position of C after the received command would be +80° in D. As +80° in D is within the reality rule range of motion of (−90°, +90°), the RRDB can return a query result indicating that the first command is reasonable. Then, after the remotely-operable device carried out the first command and moved C to +80° in D, the receipt of a second command to move by +20° in D would lead to a position of +100° in D. A position of +100° in D is outside the range of the reality rule, and so the RRDB would return a query result indicating that the second command is unreasonable.

Both operator commands and remotely-operable device feedback can be supplemented with the additional (pseudo) random signal; that is, signals that can be either random signals or pseudo-random signals such as signals generated based on input from a pseudo-random number generator. The additional signals can provide a quick and reliable detection of all erroneous and maliciously altered control and feedback messages, prevent false control and false feedback messages from being accepted and implemented, and correct erroneous messages.

In some cases, the additional signals can contain information for temporary (semi)autonomous operation of the remotely-operable device in the case of denial of service, whether benign or malicious. In an autonomous mode, the remotely-operable device is sent initial instructions or goals to carry out without human operator intervention under normal circumstance—a remotely-operable device operating in the autonomous mode can request human assistance to resolve an error or problem state. Once the remotely-operable device completes its task operating in the autonomous mode, the device can report its results and wait further instructions, perhaps after switching to a controlled mode; e.g., a mode where the remotely-operable device is operating in response to controls provided via an operator device.

In the semi-autonomous mode, a human operator is monitoring progress of the remotely-operable device using the operator device. The human operator can switch the remotely-operable device to either the autonomous mode or the controlled mode. After switching the remotely-operable device to the controlled mode, the human operator can take control of the remotely-operable device. While in the semi-autonomous mode, predictive information can be transmitted between the operator device and the remotely-operable device in real time. The transmission of predictive information can lead to opportunities for malicious attacks upon the predictive information. Such malicious attacks can be countered using herein-described techniques and methods relating to encoding information, such as the predictive information, as additional signals of commands and/or responses.

On the operator side of the interface, operators can use their knowledge and training about the physical environment and the remotely-operable device to realize when the remotely-operable device is providing unreasonable results. Components of the security system can enhance the operator's knowledge; for example, by verifying the "freshness" or currency and correctness of feedback from the remotely-operable device based on verification of the additional signals.

Tools can allow remotely-operable devices to continue mission critical tasks, even if the communication between operators and remotely-operable devices is disrupted for a longer period of time, or a malicious entity disrupts the procedure. For example, if communication is interrupted, a remotely-operable device can switch to a (semi)autonomous mode.

To enable switching to a (semi)autonomous mode, a remotely-operable device can identify a dangerous command from a presumed operator, switch to the (semi)autonomous mode, and while in the (semi)autonomous mode, prevent execution of the dangerous command. A set of system states and dangerous operator commands can be determined that, when detected, allow the remotely-operable device to block them and switch to the (semi)autonomous mode. While in the (semi)autonomous mode, the remotely-operable device can perform one or more operations of an allowed autonomous-mode set of operations. For example, while in the (semi)autonomous mode, the autonomous-mode set of operations may include commands to gather data about an environment and about the remotely-operable device and may exclude some or all movement commands.

Example Environments for Remotely Operating Devices

FIGS. 1A, 1B, 1C, and 1D each illustrate an example operating environment 100 for remotely-operable devices, in accordance with an embodiment. FIG. 1A illustrates operating environment 100 with operator environment 110 connected to remote environment 120 using network 116. Operator environment 110 can have one or more operators for controlling remotely-operable devices in remote environment 120. FIG. 1A shows n operators 112a, 112b, . . . 112n, n>0, in operator environment 110, where each of the n operators 112a, 112b, . . . 112n can utilize an operator device to send commands, such as commands in command stream 118, to device(s) in remote environment 120. In FIG. 1A, each operator 112a, 112b . . . 112n utilizes one operator device (for a total of n operator devices), and each operator device is the same. In other examples, some or all of the operators in operator environment 110 can use different types of operator devices and/or more, fewer, or different numbers of operators and/or operator devices can be utilized; e.g., each operator can use more than one operator device or more than one operator can utilize an operator device.

FIG. 1A shows that, in example remote environment 120, two types of remote devices are utilized: type "DevA" and type "DevB". In other examples, more, fewer, or different types of remote devices can be utilized. FIG. 1A also shows that there are m1 devices of type "DevA", numbered 122a, 122b, . . . 122m1, and m2 devices of type "DevB", numbered 124a, 124b, . . . 124m2. In other examples, more, fewer, or different types of remote devices can be utilized and/or more, fewer, or different numbers of each type of remote device can be utilized than shown in FIG. 1A. In still other examples, more than one network can be used to connect operator environment 110 with remote environment; e.g., one network for the "DevA" devices and another network for the "DevB" devices; different networks for different geographical regions of operator environment 110 and/or different geographical regions of remote environment 120.

After carrying out one or more commands, the device(s) in remote environment can generate one or more responses and send the response(s) in response stream 126. Each of the operator device(s) in operator environment 110 can examine response stream 126 for responses from the specific device(s) associated with the operator device.

After receiving the responses from the specific device(s) associated with the operator device in response stream 126, the operator device can provide feedback to the operator.

The feedback can include, but is not limited to, visual feedback, auditory feedback, haptic (touch-based) feedback, and/or combinations of visual, auditory, and haptic feedback. Each operator device in operator environment 110 and each device in remote environment 120 can be and/or include a computing device, such as discussed below in more detail in the context of at least FIG. 4B.

In some examples, part or all of the communication between operating environment 110 and remote environment 120 can be secured. FIG. 1A shows p security devices (SDs) 114a . . . 114p in operating environment 110, where security devices 114a, 114 are respectively configured to secure communications between operators 112a, 112n and remote environment 120. In the example shown in FIG. 1A, communications between operator 112b and remote environment are not secured by a security device; as such, these communications may be unsecured. In other examples, security device 114 can be part of an operator device, network 116, and/or a remote device. In still other examples, such as shown in FIG. 1A, security device 114a, 114n, can be a separate device from either an operator device, network 116, or a remote device. For example, security device 114a can be a plug-and-play type device; e.g., a dongle or other device connected to an operator device with a Universal Serial Bus (USB) or similar cable, a card operating according to IEEE 1394 (e.g., a PCMCIA card), or other removable device connected to the operator device for operator 112a.

In some examples, operator environment 110 and remote environment 120 can overlap or be the same. For example, a remote device can be configured to carry the operator into the remote environment; e.g., the remote device can be an underwater submersible, a space device, or a walking robot. As another example, the operator environment 110 and remote environment 120 may be separated by a small physical space; e.g., a wall of a lab, power plant, or hazardous environment. Many other examples of operator devices, operators, operating environments, networks, remote devices, and remote environments are possible than described herein.

In some embodiments, additional signals can be encoded and added to command stream 118 and/or response stream 126; e.g., the additional signals are transmitted "in-band" with command stream 118 and/or response stream 126. For example, the additional signals in command stream 118 can be and/or include (pseudo)random signals that contain unique information added by operators 112a, 112b . . . 112n. Similar (pseudo)random signals can be encoded by some or all of remotely-operable devices 122a, 122b . . . 122m1 and/or 124a, 124b . . . 124m2 and added to messages in response stream 126. These additional signals can be configured to be difficult to detect by being encoded in various portions of messages, being encoded in some but not other messages, and/or by being transmitted using a known secure channel that is separate from command stream 118 and/or response stream 126.

The additional (pseudo)random signals can be used to: (i) verify the content and the freshness of exchanged messages; (ii) recover the content of possibly corrupted data, (iii) verify reasonableness of a command; and (iv) enable the remote manipulator to switch to an autonomous operating mode and/or execute default command(s). For verification of content and freshness of messages, the additional signals can include, for example, timing information, message sequencing information, message size information, parity check data, and/or check sum data. Parity checking and/or check sum data can be used to recover corrupted data as well.

To verify the reasonableness of a command, operator 112a, 112b . . . 112n and/or security devices 114a . . . 114p can determine predictive information for the remotely-operable device. Once determined, the predictive information can be encoded as one or more (additional) signals in command stream 118. An example of predictive information for a remotely-operable device ROD is a future status. A future status for remotely-operable device ROD is a status predicted for ROD after ROD at least partially executes one or more commands. As an example of a future status, suppose a remotely-operable device, such as remotely-operable device 122a is headed in a direction of 90° and receives a command to change its heading by +30°. Then a future status of a heading of remotely-operable device 122a is 120°. As another example, if remotely-operable device 122a is moving at a speed of X meters/second (m/s) and receives a command to increase speed by 0.2X m/s, then the future status of a speed of remotely-operable device 122a is 1.2X m/s.

As a third example, suppose remotely-operable device 122a is moving at a speed of X meters/second (m/s) along a heading of 45° moving at Y m/s. Then, if remotely-operable device 122a receives command Cα to reduce speed by 0.8Y m/s and command Cβ to change the heading by −23°, then future statuses for remotely-operable device 122a include: a future status of a speed of 0.2Y m/s after completely executing command Cα, a future status of a heading of 22° after completely executing command Cβ, and a future status of a velocity of 0.2 m/s along a heading of 22° (or separate speed and direction future statuses) after completely executing commands Cα and Cβ.

In some embodiments, the future status can be encoded in an additional signal for a command message applicable to the command sent in the command message; e.g., if command message CM0 conveys command C0 with a future status of FS0, then a body of message CM0 can include C0 and art additional signal associated with CM0 cart encode FS0. In other embodiments, future status FS0 can be included in the body of message CM0.

In even other embodiments, the future status can be applicable to a command other than a command sent in a command message. For example, an operator can be configured to send a command that is expected to be executed either conditionally or at a later time. Then, if the condition arises or the later time is reached, the remotely-operable device can determine a future status for the conditional/delayed command based on conditions after the condition arises or the later time is reached. As another example, future statuses cart be delayed and/or transmitted for only some commands—e.g., if a series of movement commands were to be executed, the future status can be calculated at certain points, such as a beginning of the series of movement commands, at a waypoint reached in the series of movement commands, and/or at an end of the series of movement commands.

As still another example, the future statuses can be sent offset from the commands to possibly confuse an attacker; e.g., if the operator knows a remotely-operable device buffers commands or there is a delay in calculating future statuses on the remotely-operable device, then a future status for a command can be sent in a command message for a later command sent later than the command. For example, suppose the future status FSC for a command C is sent in the subsequent command message. Then, let the next four commands to a remotely operable device be C1, C2, C3, and C4 with corresponding future statuses FS1, FS2, FS3, and FS4. Then the next five command messages would include:

message 1 including C1; message 2 including C2 and an additional signal encoding FS1; message 3 including C3 and an additional signal encoding FS2; message 4 including C4 and an additional signal encoding FS3; and message 5 including an additional signal encoding FS4. Many other examples of future statuses are possible as well.

Upon receipt of a command, a remotely-operable device can also calculate the future status of the command. Then, if the future status calculated by the remotely-operable device is within a permitted range of error as the received future status, then the command can be considered to be transmitted accurately. Continuing the example above, if remotely-operable device 122a is headed in a direction of 93° and receives a command to change its heading by +30°, then a calculated future status of a heading of remotely-operable device 122a is 123°, which would be 3° different than a received future status of 120° as discussed above. If the permitted range of error was ±5°, then the command can be considered to be have been transmitted accurately.

A command whose received future status matches a calculated future status can be considered a priori to be reasonable. In some embodiments, a remotely-operable device can determine a reasonableness of the command as well. FIG. 1A shows each remotely-operable device 122a, 122b ... 122m1 and 124a, 124b, ... 124m2 with a respective reality-rules database (RRDB) 122c, 122d ... 122e and/or 124c, 124d ... 124e. Each reality-rules database can store one or more reality rules for the remotely-operable device, where each reality rule relates to a constraint on the remotely-operable device.

In some scenarios, the reality-rules database is not transmitted, even in part, during operation of a remotely-operable device. Rather, while the remotely-operable device is operating, the reality-rules database is treated as a secret; i.e., a codebook about the remotely-operable device and its operating environment. As such, no information in the secret reality-rules database is transmitted during operation. In some embodiments, the remotely-operable device can be configured to ensure secrecy of the reality-rules database; e.g., by use of encryption, tamperproof devices for storage of the reality-rules database, and/or other security mechanisms.

Example reality rules include, but are not limited to, rules about: range(s) of motion of part or all of the remotely-operable device, range(s) of speeds and/or velocities of part or all of the remotely-operable device, range(s) of accelerations for part or all of the remotely-operable device, a rule about a location for operating the remotely-operable device, location(s) for operating part or all of the remotely-operable device, location(s) for not operating part or all of the remotely-operable device a rule about a stress on the component, range(s) of stresses on part or all of the remotely-operable device, distances between components of the remotely-operable device, and distances between remotely-operable devices. Many other example reality rules, include other example reality rules disclosed herein, are possible as well.

For example, if remotely-operable device 122a is designed to move at speeds between 0 and 5 m/s then a reality rule in reality-rules database 122c can include a rule specifying that the speed of remotely-operable device 122a is constrained to be between 0 and 5 m/s. Reality rules can also include rules about future statuses; e.g., a reality-rule can specify that a difference between a calculated future status for a heading and a received future status for a heading must be between −5° and +5° to be reasonable.

In some cases, a threshold can be used to determine reasonableness. For example, if remotely-operable device 122a is designed to move at speeds between 0 and 5 m/s, then a reality rule in reality-rules database 122c can include a rule specifying that the speed of remotely-operable device 122a is constrained less than a threshold of 5 m/s. Continuing this example, at time t0, let remotely-operable device 122a be moving at 2 m/s. If a command Cs1 is received by remotely-operable device 122a at t0 to speed up by 4 m/s, then a future status FSs1 would be that remotely-operable device 122a would be moving at 6 m/s, and so based on the 5 m/s threshold of the reality-rule, then remotely-operable device 122a can determine that Cs1 is unreasonable.

In some cases, a command can be reasonable if partially executed. Again let remotely-operable device 122a move at 2 m/s. If a command Cs2 is received by remotely-operable device 122a at t0 to speed up by 1 m/s for each of four seconds, then remotely-operable device 122a can partially execute the command by speeding up by 1 m/s until reaching 5 m/s, at which point, remotely-operable device 122a can determine the remainder of command Cs2 is unreasonable based on the above-mentioned 5 m/s threshold (or 0 to 5 m/s range) and stop executing Cs2. Similarly for previously-mentioned command Cs1 to speed up by 4 m/s, remotely-operable device 122a can partially execute Cs1 by speeding up from 2 m/s to 5 m/s, reach the threshold, and stop executing command Cs1.

As another example, while operating in remotely-operable device 122a in remote environment 120, remotely-operable device 122a can be permitted to move in certain headings and not in other headings depending on a current location of the device. For example, suppose that remotely-operable device 122a is not permitted to head south from its current location, where south is defined based on a range of headings [HS1, H2]. Then, let remotely-operable device 122a receive a command Cs3 to change its heading by X°, where changing its heading by (X/2)° would put the device within the [HS1, HS2] range of headings. Remotely operable device 122a can determine the future status of command Cs3 and either reject Cs3 as being unreasonable as Cs3 would have the device head south or partially execute the command by changing the heading of the device by slightly less than (X/2)°. The partially executed command can be determined to be reasonable but only partially executed, partially (un)reasonable, or unreasonable but partially executable. Many other examples of using thresholds to determine reasonability of commands and/or partial execution of commands are possible as well.

Multiple reality rules can apply to one command. Continuing the heading example, once a difference in calculated and received futures statuses for a heading is determined to be reasonable, then the heading and/or the future status of the heading can be checked for reasonableness as well. As another example, suppose a command was received to move a component of a remotely-operable device by 5 units in an X direction and 3 units in a Y direction, then reality rules applicable to movement of the component in the X direction, movement of the component in the Y direction, and perhaps, for the net movement of the component in the XY direction, can be used to determine reasonableness of the movement command.

A reasonableness value for a command can be transmitted from a remotely-operable device to an operator via response stream 126; e.g., encoded in a feedback message that is sent in response stream 126 to the operator. The reasonableness value can be expressed as a binary value (e.g., 1=reasonable, 0=unreasonable), a numeric value, an alphabetic value, an alphanumeric value, and/or otherwise expressed. Then, upon receipt by the operator, the reasonableness value can be used as feedback on the command stream to indicate the correctness, or lack thereof, of commands in command stream 118 and/or of the security of command stream 118.

In some embodiments, the feedback message and/or additional signals can also include information about command(s) determined to be unreasonable; e.g., message identifiers, command identifiers, time(s) of reception of unreasonable commands, indication(s) of reason(s) for finding command(s) to be unreasonable, reality-rule identifier(s) used to find the command(s) unreasonable, and combinations thereof. Feedback about an unreasonable command can be provided in response to reception of an unreasonable command and/or as part of a report, log, or other record of unreasonable command(s). In some embodiments, the operator can request that the remotely-operable device provide part or all of a record of unreasonable command(s); e.g., during system maintenance; in response to finding a specific command unreasonable where the remotely-operable device does not otherwise provide feedback on unreasonable commands. The requested record can be provided by the remotely-operable device as additional signal(s) encoded into feedback 126.

In other embodiments, an operator device can determine reasonableness of feedback. One technique to determine reasonableness of feedback can be based on previously-provided commands. For example, suppose a command was sent by an operator device to move a component of a remotely-operable device by 5 units in an X direction and 3 units in a Y direction. Some time after completion of the command, the operator device can received feedback from the remotely-operable device indicating that the command was carried out.

In this example, the feedback information that the remotely-operable device moved 4.95 units in the X direction and 3 units in the Y direction. The operator device can determine if the feedback matches, or nearly matches the action specified in the command—in this example, the remotely-operable device missed performing the specified command by 0.05 units in the X direction.

In some embodiments; e.g., driving a bulldozer, this 0.05 unit difference may be reasonable; while in other embodiments; e.g., operating a surgical manipulator or an electron microscope, this 0.05 unit difference may be unreasonable. The operator device can determine the reasonableness of differences between commands and feedback based on threshold values; e.g., a threshold difference in unit values, a threshold percentage difference, or a threshold based on sonic other value. In other embodiments, the operator device can be configured with its own reality rules and/or reality-rules data base for determining reasonableness of feedback; e.g., rules specifying the thresholds of differences between commands and feedback mentioned just above.

In still other embodiments, the operator device can be configured with a copy of the RRDB provided to the remotely-operable device and can independently calculate the reasonableness of previously-provided commands using the techniques discussed above. In even other embodiments, the operator device can determine that feedback is unreasonable and generate a notification to the operator that feedback is (potentially) unreasonable. The operator can then review the notification, the feedback, and/or other information to decide whether any action need be taken based on the (possibly) unreasonable feedback. In still even other embodiments, the operator device can be configured to take action after determining feedback is unreasonable; e.g.,
generate commands to correct differences between previously-provided command(s) and corresponding feedback. Continuing the example above, the operator device can determine that the above-mentioned 0.05 unit difference in the X dimension is unreasonable based on its own reality rules and/or thresholds, generate a command to a remotely-operable device to move 0.05 units in the X dimension, and then send the generated command to the remotely-operable device.

A backup command can be encoded as an additional signal of command stream 118. If a command is determined to be unreasonable, the backup command can be executed. For example, if a remotely-operable device receives a command CM1 to move along a designated heading, a backup command can be to stop the remotely-operable device, as the likely reason command CM1 is unreasonable is that the remotely-operable device is being directed to a restricted area or region where the device is not supposed to operate.

A remotely-operable device can, when presented with an unreasonable command, enter into a (semi)autonomous mode. While in the (semi)autonomous mode, the remotely-operable device can utilize some or all of the functionality of the remotely-operable device. For example, while in the (semi)autonomous mode, the remotely-operable device may be able to move itself, but can perform all other functions of the remotely-operable device. As another example, suppose a particular component of the remotely-operable device is potentially dangerous to operate without human control. Then, the remotely-operable device may be instructed not to use the particular component while in (semi)autonomous mode. Many other examples of operation of the remotely-operable device in an autonomous or semiautonomous mode are possible as well.

In some embodiments, one or more reality rules can control (semi)autonomous mode operation. For example, suppose reality rule(s) specified that the remotely-operable device can reasonably move at speeds between 0 and 5 m/s, while in a controlled (normal operating) mode, and move at speeds between 0 and 2 m/s while in a (semi)autonomous mode. As another example, suppose reality rule(s) specified that the remotely-operable device can reasonably move within 1 meter of a restricted region of remote environment 120 while in the controlled mode, and move within 5 meters of the restricted region while in the (semi)autonomous mode.

As a further example, the remotely-operable device can be configured to operate in the (semi)autonomous mode until the remotely-operable device is at a safe stop position when benign failures and malicious activates are detected. The safe stop position, and other positions, can be determined using virtual fixtures; e.g., specifications of dimensions of forbidden region(s) and/or allowable (not forbidden) regions. Then, operating until reaching a safe stop position can involve moving the remotely-operable device autonomously until the remotely-operable device is in an allowable region as defined by the virtual fixtures. Once in the allowable region, the remotely-operable device can partially or completely shut down; e.g., come to a safe stop.

In some embodiments, the remotely-operable device can receive feedback about classifying commands as reasonable and/or unreasonable. A reality-rules database and/or other aspects of the remotely-operable device can be modified based on this feedback. For example, if commands instructing a remotely-operable device to operate safely are determined to be unreasonable by the remotely-operable device, then the reality-rules database can be modified to enable the remotely-operable device to determine the commands are reasonable.

In some scenarios, the remotely-operable device may be knowingly commanded to operate in an unreasonable fashion; e.g., during an emergency. As such, the remotely-operable device can be configured to operate in an emergency mode. During the emergency mode, some or all reasonableness checks can be disabled to permit the operator(s) of the remotely-operable device to command as necessary without being overridden by the remotely-operable device. For example, suppose a remotely-operable device was configured with a temperature sensor and a reality-rule database with a rule RT indicating the remotely-operable device can operate in temperatures in a [−40° F., +160° F.] range. If the remotely-operable device then receives a command to enter into a burning building during an emergency, the temperature sensor can indicate that the remotely-operable device is being commanded to move into a region where the temperature is greater than +160° F., and so determine the command is unreasonable based on rule RT. However, if the remotely-operable device is operating in an emergency mode, the commands may not be subject to reasonableness checks and/or rule RT can be ignored, and so the remotely-operable device can carry out the command to move into the burning building.

In some embodiments, the emergency mode can be entered only after a series of signals and/or commands are received to make entry into the emergency mode difficult to be entered into either accidentally or maliciously. For example, entry in to the emergency mode can be rejected as unreasonable when for a number N of requests, e.g., N=2 or 4, before entering into the emergency mode upon the N+1'st request. Rejecting a number of requests before eventual acceptance can discourage malicious emergency-mode entry and reduce the likelihood of accidental emergency-mode entry. As another example, a single-use emergency-mode secret can be transmitted from the operator as part of a command requesting emergency-mode entry. Upon receipt of the command, the remotely-operable device can compare the transmitted secret to an emergency-mode secret stored on the remotely-operable device; e.g., stored in a reality-rules database treated as a secret. Then, if the received secret matches the transmitted secret, then the remotely-operable device can enter into the emergency mode.

In other embodiments, the transmitted secret can itself be encrypted; e.g., using public-key encryption. Then, upon reception of the encrypted transmitted secret, the remotely-operable device can decrypt the received secret and then compare the received and decoded secret with the stored secret. Other key-exchange techniques can be used instead or as well to share a secret, such as but not limited to the emergency-mode secret, between the operator and the remotely-operable device.

In still other embodiments, single-use secrets can be used to enable other normally protected operations for the remotely-operable device. As one example, a single-use RRDB-download secret can be transmitted from the operator device as part of a command requesting that the remotely-operated device download a copy of the RRDB to the operator device. A related example can include a single-use RRDB-upload secret can be transmitted from the operator device as part of a command requesting that the remotely-operated device accept uploading of a copy of a RRDB from the operator device; e.g., to correct the RRDB. In some embodiments, the RRDB-upload secret can be sent by the remotely-operable device to the operator device to request a copy of the RRDB; e.g., the remotely-operable device determines the RRDB has become corrupted, yet requires the RRDB for continued operation, and so the remotely-operable device sends the RRDB-upload secret as part of a request for a fresh copy of the RRDB.

As another example, a single-use RRDB-modification secret can he transmitted from the operator device as part of a command requesting one or more modifications to the RRDB. If the RRDB-modification mode secret is accepted by the remotely-operable device, then the remotely-operable device can send a RRDB-modification notification to the operator device that the RRDB can be modified. After receiving the RRDB-modification notification, the operator device can send database commands to review, update, delete, and/or insert reality-rule(s) in the RRDB. In particular embodiments, acceptance of the RRDB-modification mode secret enables an editing session to make multiple updates to the RRDB once the editing session is completed, modifications are no longer permitted. In other embodiments, acceptance of the RRDB-modification mode secret enables making a predetermined maximum number Max-Mods of modifications to the RRDB; e.g., MaxMods=1, 5, 10, or some other number.

In even other embodiments, an operation, such as but not limited to, RRDB upload, RRDB download, and/or RRDB modification, can be proposed by one device (e.g., the operator device), and verified by the other device (e.g., the remotely-operable device) one or more times before finding the request to be reasonable. Finding the operation to be reasonable can involve one or more exchanges of messages between the remotely-operable device and the operator device; these exchanges can allow negotiation of the request (e.g., download or upload only a portion of the RRDB, setting the above-mentioned MaxMods value) and/or verification of the proposed request. For example, an operation can be rejected as unreasonable for a number N of requests, e.g., N=2 or 4, before finding the operation as validated upon the N+1'st request.

Rules within a reality-rule database for a remotely-operable device can be configured with one or more indicators that indicate applicability of the rule based on a mode of the remotely-operable device. For example, the above-mentioned rule RT can have indicators that rule RT is applicable while the remotely-operable device is operating in a controlled mode or a (semi)autonomous mode, but not while the remotely-operable device is operating in an emergency mode. Many other examples of operating modes and corresponding indicators are possible as well.

Figure 1B:
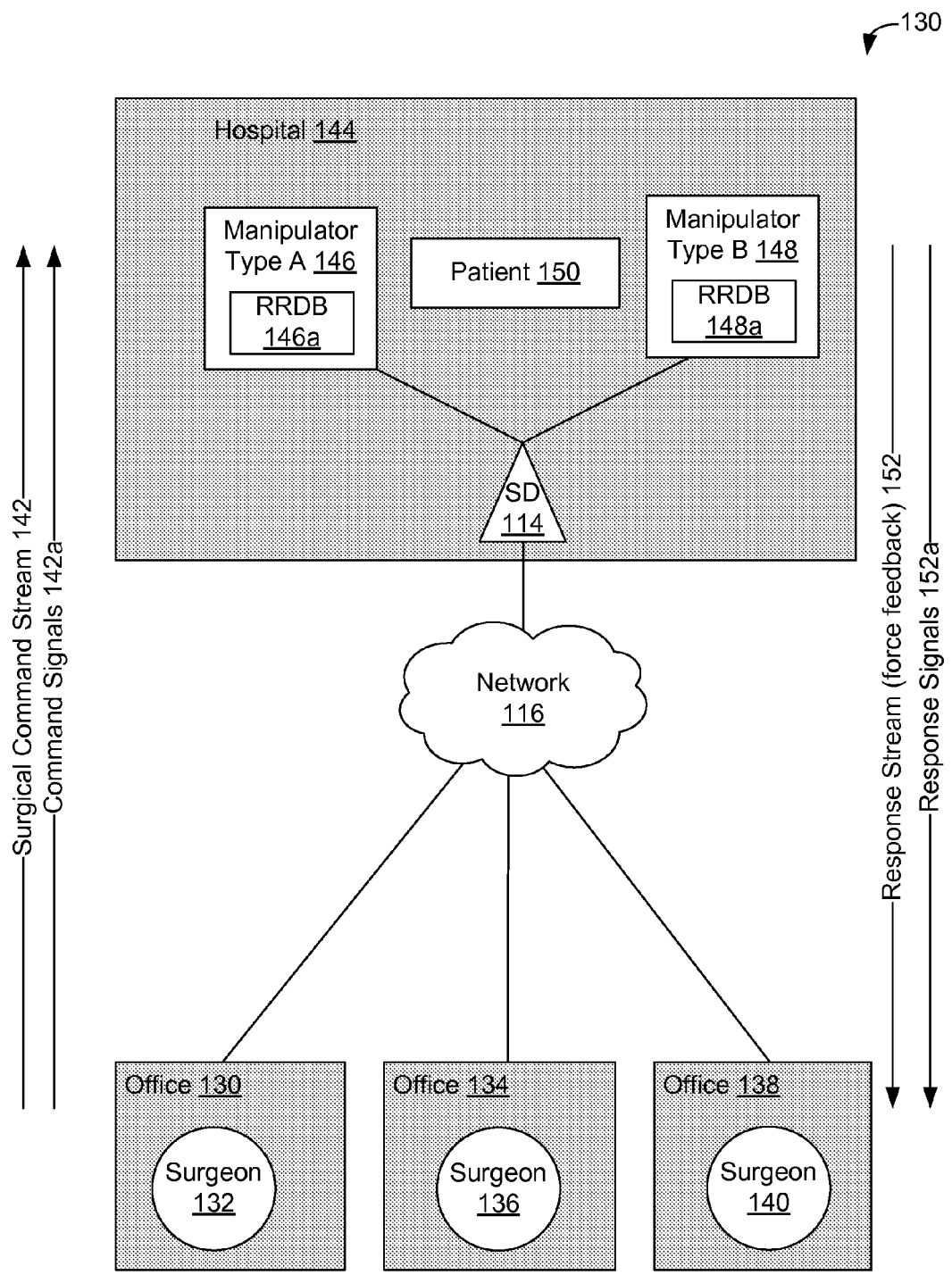

FIG. 1B illustrates operating environment 130 with offices 130, 134, 138 making up the operator environment 110 connected to remote hospital 144 using network 116. For example, operators 132, 136, and 140 (e.g., surgeons and/or other medical personnel) can remotely operate on patient 150 in hospital 144 using surgical manipulators 146, 148 as remotely-operable devices. FIG. 1B shows two types of surgical manipulators: type A 146, and type B 148. In some examples, one type of surgical manipulator can be used in a remote operation; in other examples, more than two types of surgical manipulators can be used in a remote operation; and in even other examples, remotely-operable devices other than surgical manipulators can be used in a remote operation; e.g., lighting devices, anesthetic equipment, diagnostic equipment, etc. In still other examples, medical procedures other than operations can be performed remotely; e.g., diagnoses, examinations, observations.

Each respective office 130, 134, 138 has a respective operator 132, 136, 140 having one or more operator devices for controlling manipulators 146, 148 in hospital 144. Each operator device can send surgical commands in surgical command stream 142 via network 116 and security device 114 in hospital 144 to manipulators 146 and/or 148. In response to surgical commands in surgical command stream 142, manipulators 146, 148 can send responses in response stream 152 to operators 132, 136, and/or 140 via security device 114 and network 116. Responses in response stream 152 can include, but are not limited to feedback to operators 132, 136, and/or 140; e.g., visual feedback, auditory feedback, haptic (touch-based) feedback, and/or combinations of visual, auditory, and haptic feedback.

As shown in FIG. 1B, surgical command stream 142 is accompanied by additional command signals 142a. In sonic embodiments, surgical command stream 142 can be transmitted separately from command signals 142a; e.g., additional command signals 142a are transmitted out-of-band with respect to surgical command stream 142. As also shown in FIG. 1B, response stream 152 is accompanied by additional response signals 152a; e.g., additional response signals 152a are transmitted out-of-band with respect to response stream 152. Signals in additional command signals 142a and additional response signals 152a can include some or all of the (pseudo)random signals and additional signals discussed above in the context of at least FIG. 1A.

FIG. 1B illustrates that each manipulator 146, 148 is configured with a respective reality-rules database 146a, 148a. Reality-rules databases and reality rules are discussed above in more detail in the context of at least FIG. 1A. Manipulator 146 and/or manipulator 148 can be configured to perform some or all of the features of a remotely-operable device discussed above in the context of at least FIG. 1A. Also, some or all of operators 132, 136, and 140 can be configured to perform some or all of the features of an operator as discussed above in the context of FIG. 1A.

Figure 1C:
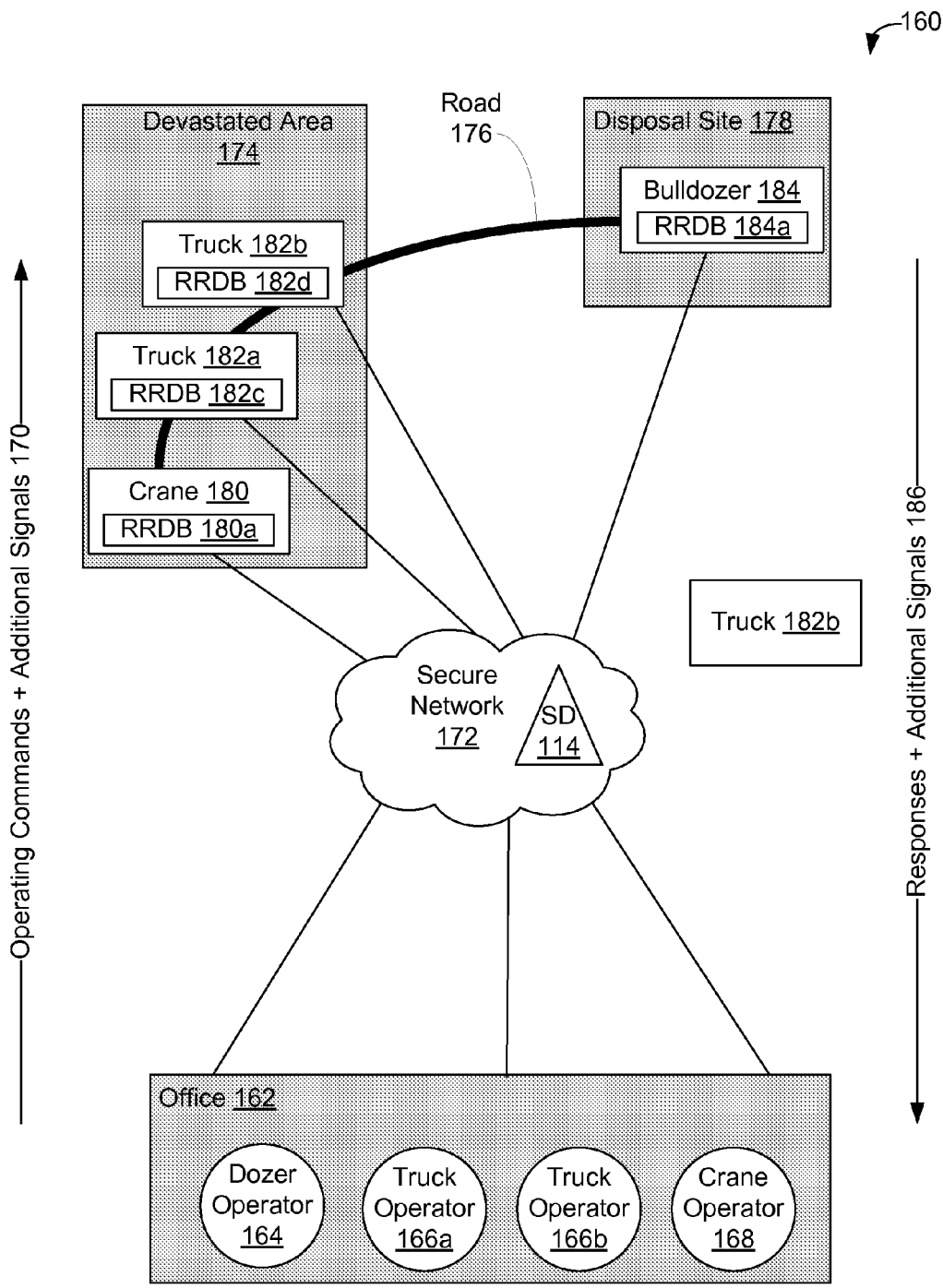

FIG. 1C illustrates operating environment 160 with office 162 acting as the operator environment connected to remote devastated area 174, road 176, and disposal site 178 using network 172. Office 162 has four operators controlling respective remotely-operable devices: bulldozer (dozer, for short) operator 164 for operating remote bulldozer 184, truck operators 166a, 166b for operating respective remote trucks 182a, 182b, and crane operator 168 for operating crane 180.

The four operators and associated operator devices can restore devastated area 174 by providing commands for loading materials into trucks 182a, 182b using crane 180 and carrying the materials away from devastated area 174 on road 176 to disposal site 178. In some examples, one or two types of equipment can be used in construction operation, such as, but not limited to, restoring a devastated area, hazardous waste cleanup, landmine detection and removal, undersea building, remote construction, etc. In other examples, more than three types of equipment can be used in a remote construction operation; and in even other examples, remotely-operable devices other than construction equipment, such as cranes, trucks, and bulldozers, can be used in an remote construction operation; e.g., demolition equipment, welding, fabrication and assembly equipment, test equipment, etc.

Each operator device operated in office 162 can send operating commands 170 via secure network 172. Secure network 172 can include one or more security devices 114 configured for securing communications between office 162, devastated area 174, road 176, and disposal site 178, such as but not limited to communications including operating commands 170 and/or responses 186. For example, suppose bulldozer operator 164 is utilizing an operating device configured for voice communications to disposal site 178. In this example, secure network 172 and/or security device 114 can be configured to encrypt or otherwise secure voice communications between office 162 and disposal site 178.

In response to operating commands 170, crane 180, tracks 182a, 182b, and/or bulldozer 184 can send responses 186. Responses 186 can include, but are not limited to feedback to operators 164, 166a, 166b, and/or 168; e.g., visual feedback, auditory feedback, haptic (touch-based) feedback, and/or combinations of visual, auditory, and haptic feedback.

As shown in FIG. 1C, operating commands 170 are accompanied by additional signals, such as the additional signals transmitted in-band with command stream 118 of FIG. 1A. As also shown in FIG. 1C, responses 186 are accompanied by additional signals, such as the additional signals transmitted in-band with response stream 126 of FIG. 1A. Additional signals in operating commands 170 and responses 186 can include some or all of the (pseudo) random signals and additional signals discussed above in the context of at least FIG. 1A.

FIG. 1C illustrates that each of crane 180, trucks 182a, 182b, and bulldozer 184 is configured with a respective reality-rules database 180a, 182c, 182d, and 184a. Reality-rules databases and reality rules are discussed above in more detail in the context of at least FIG. 1A. Crane 180, trucks 182a, 182b, and bulldozer 184 can be configured to perform some or all of the features of a remotely-operable device discussed above in the context of at least FIG. 1A. Also, some or all of operators 164, 166a, 166b, and 168 can be configured to perform some or all of the features of an operator as discussed above in the context of FIG. 1A.

Figure 1D:
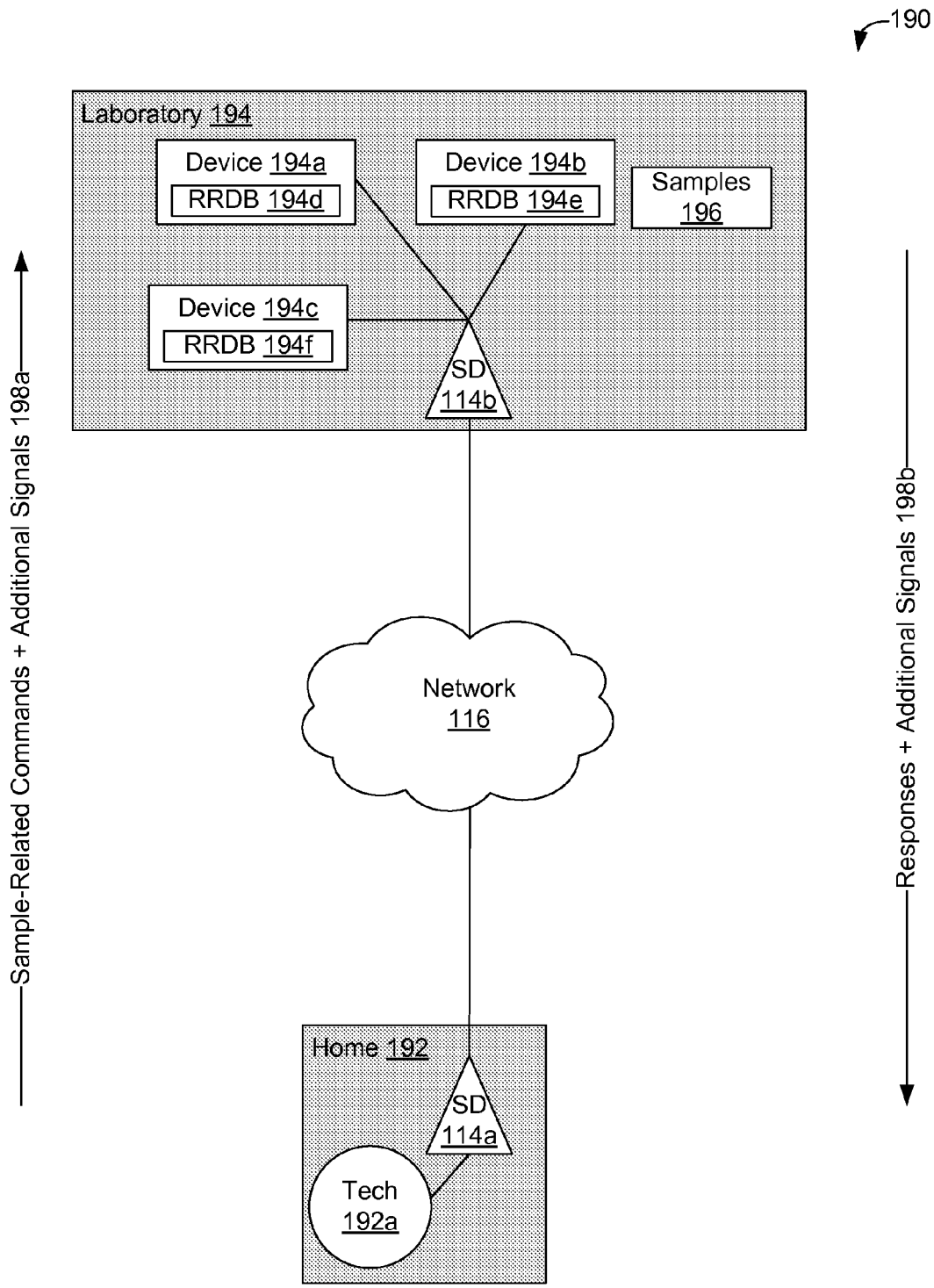

FIG. 1D illustrates operating environment 190 with home 192 as the operator environment connected to remote laboratory 194 using network 116. For example, technician (tech for short) 192a can remotely perform experiments on samples 196 in laboratory 194 using remote devices 194a, 194b, 196c. In some examples, more or fewer than three devices can be used for remote laboratory experiments. In other examples, other procedures and experiments can be performed remotely; e.g., testing, observation, etc.

Home 192 includes technician 192a with one or more operator devices for controlling devices 194a, 194b, and 194c. Each operator device can send sample-related commands 198a via security device 114a in home 192, network 116, and security device 114b in laboratory 194 to devices 194a, 194b, and/or 194c. In response to sample-related commands 198a, devices 194a, 194b, 194c, can send responses 198b to an operating device utilized by technician 192a via security device 114b, network 116, and security device 114a. Responses 198b can include, but are not limited to feedback to technician 192a; e.g., visual feedback, auditory feedback, haptic (touch-based) feedback, and/or combinations of visual, auditory, and haptic feedback.

As shown in FIG. 1D, sample-related commands 198a are accompanied by additional signals, such as the additional signals transmitted in-band with command stream 118 of FIG. 1A. As also shown in FIG. 1D, responses 198b are accompanied by additional signals, such as the additional signals transmitted in-band with response stream 126 of FIG. 1A. Additional signals in sample-related commands 198a and responses 198b can include some or all of the (pseudo)random signals and additional signals discussed above in the context of at least FIG. 1A.

FIG. 1D illustrates that each device 194a, 194b, 194c is configured with a respective reality-rules database 194d, 194*e*, 194*f*. Reality-rules databases and reality rules are discussed above in more detail in the context of at least FIG. 1A. Some or all of devices 194*a*, 194*b*, and 194*c* can be configured to perform some or all of the features of a remotely-operable device discussed above in the context of at least FIG. 1A. Also, tech 192*a* can be configured to perform some or all of the features of an operator as discussed above in the context of FIG. 1A.

Example Constraints on Remotely-Operable Devices

Figure 2A:
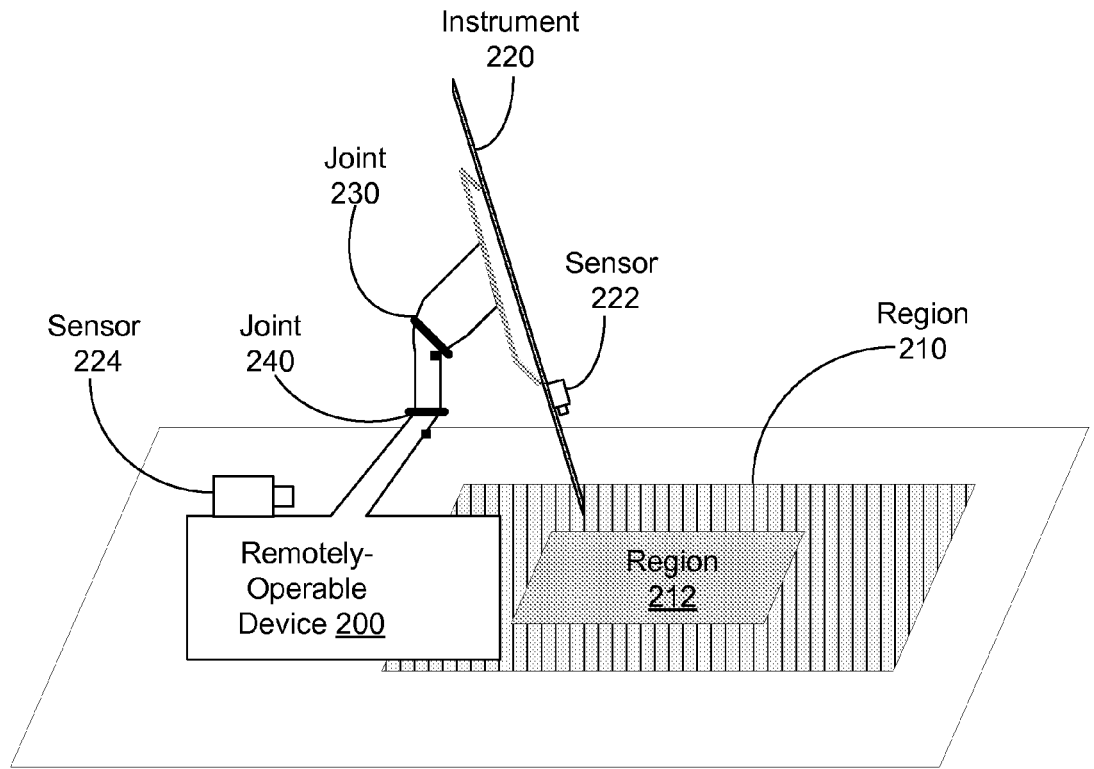
FIG. 2A illustrates an example remotely-operable device operating in an environment, in accordance with an embodiment.

FIG. 2A illustrates remotely-operable device 200 operating in region 210, which in turn includes a smaller region 212, in accordance with an embodiment. Remotely operable device is configured with sensor 224 and can move at joints 230 and 240 to manipulate instrument 220. Sensor 222 can be configured to provide information about instrument 220. For example, sensor 222 and/or 224 can be or include a camera. Many other examples of sensors 222 and/or 224 are possible as well. In some scenarios, remotely-operable device 200 can include reality-rules database 226. Reality-rules database 226 can include rules about constraints on remotely operable device.

Features of the environment and of remotely-operable device 200 can place constraints on operating the device. Example constraints from features of the environment include a constraint to remain within region 210, a constraint not to enter region 212, or a constraint to maintain a tip of instrument 220 above region 212. Many other constraints from features of the environment are possible as well.

In some embodiments, constraints from features of the environment can be observed using sensors configured for observing the environment; e.g., sensors 222, 224. Based on information from the sensors configured for observing the environment, remotely-operable device 200 and/or an operator (not shown in FIGS. 2A and 2B) can determine whether constraints from features of the environment are being enforced.

Figure 2B:
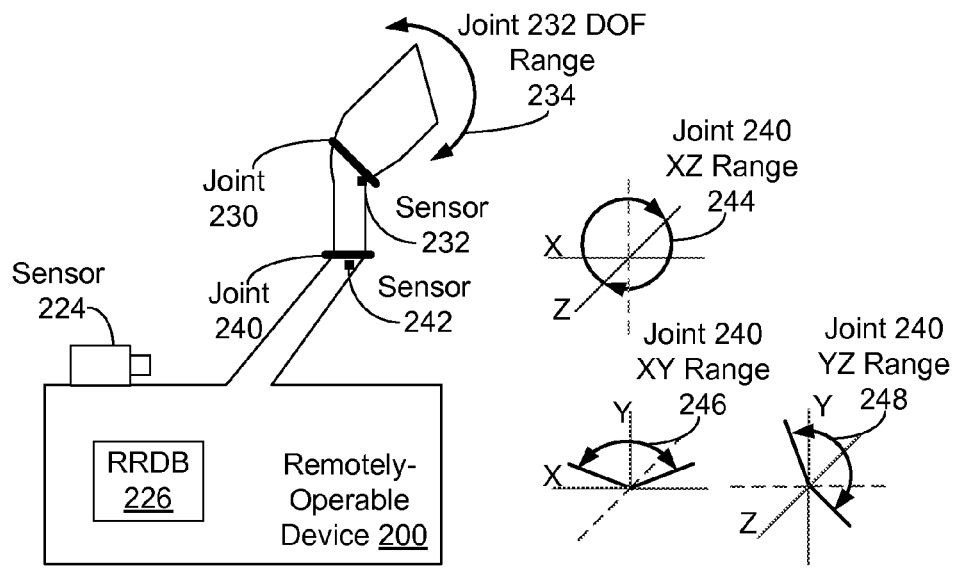
FIG. 2B illustrates example constraints on components of the remotely-operable device illustrated in FIG. 2A, in accordance with an embodiment.

FIG. 2B illustrates example constraints on components of remotely-operable device 200, in accordance with an embodiment. One example constraint is that joint 230 of remotely-operable device 200 operate with one degree of freedom (DOF) within a range 234 of approximately 180°.

Three example constraints for joint 230 of remotely-operable device 200 are illustrated in FIG. 2B. One constraint is range 244 of movement about a Y axis (shown as a dashed line for range 244) in an XZ plane for rotations within a 360° range; e.g., remotely-operable device 200 can rotate freely about the Y axis. A second constraint is range 246 of movement about a Z axis (shown as a dashed line for range 246) in an XY plane within an approximately 160° range permitting movement within approximately 80° on either side of the Y axis. A third constraint is range 248 of movement about an X axis (shown as a dashed line for range 248) in a YZ plane to rotations within an approximately 180° range with movement permitted within from about −20° to about 160° with respect to the Y axis.

Each of these example constraints on joints 230 and 240 can be observed using sensors configured for observing remotely-operable device. For example, sensor 232 can be configured to observe motion of joint 230 and sensor 242 can be configured to observe motion of joint 240. In some embodiments, sensor 232 and/or sensor 242 can be configured to observe rates of motion (e.g., velocities, accelerations), stresses, temperatures, and/or other conditions related to joints 230 and/or 240. Based on these observations, additional constraints can be determined for remotely-operable device. Some or all of the constraints for remotely-operable device 200 can be stored as reality rule(s) in reality-rule database 226, such as discussed above in the context of at least FIG. 1A.

Example Security Device Operating Scenario

Figure 3:
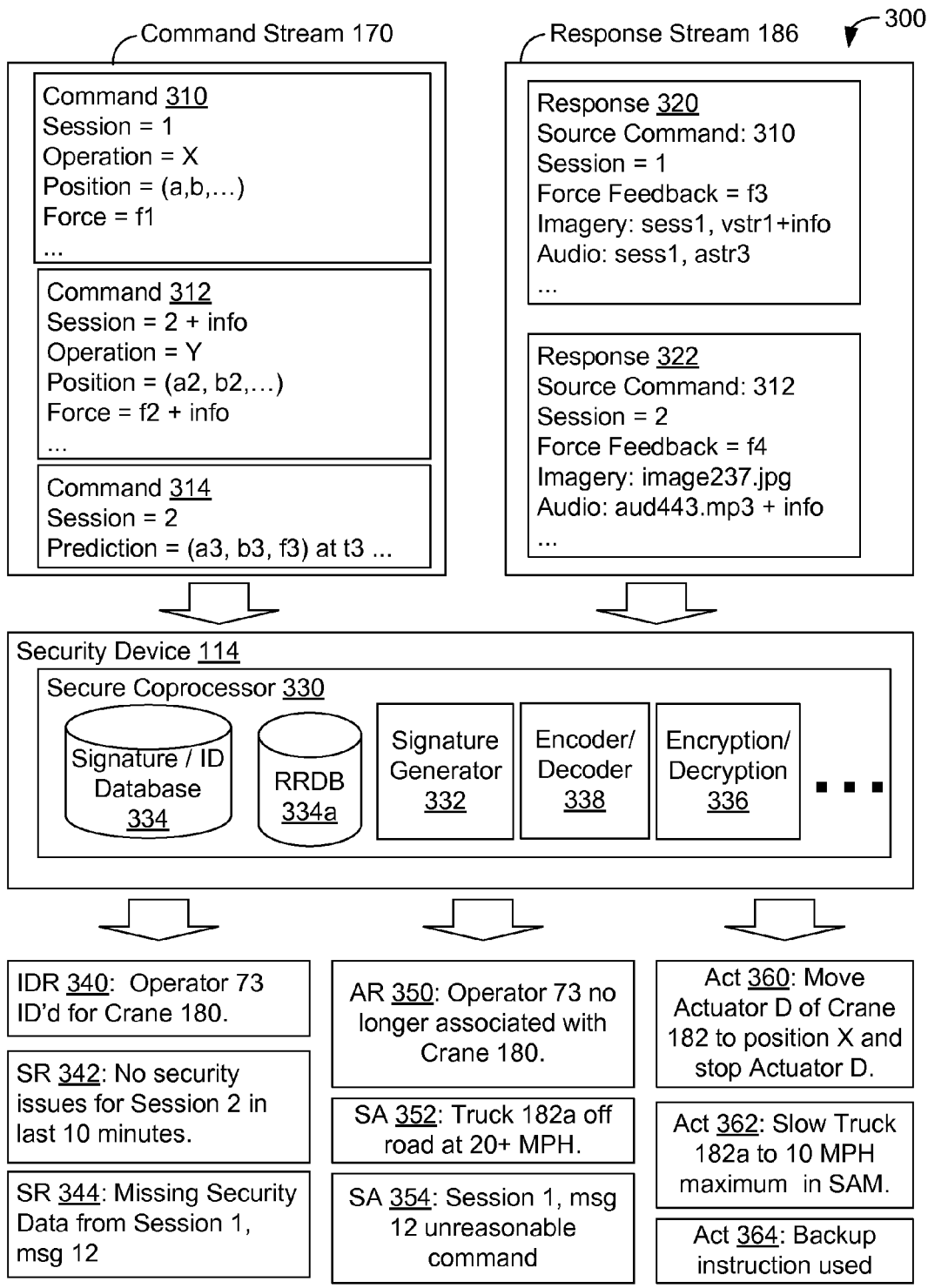
FIG. 3 illustrates an example scenario for operating a security device, in accordance with an embodiment.

FIG. 3 illustrates example scenario 300 for operating security device 114 in operating environment 160 shown in FIG. 1C, in accordance with an embodiment. Scenario 300 begins with at security device 114 receiving at least two inputs—command stream 170 and response stream 186. FIG. 3 shows two example commands in command stream 170: command 310 for an operating session "1" to perform an operation of "X" at position "(a, b, . . . )" with force "f1" and command 312 for an operating session "2" to perform an operation of "Y" at position "(a2, b2, . . . )" with force "f2".

Command 312 also has two additional signals encoded in fields of the command: additional signal "AS1*a*" encoded within a session field of the command and additional signal "AS1*b*" encoded within a force field of the command. Encoding additional signals within fields of messages is discussed in more detail in the context of at least FIG. 4. In other scenarios, more, different and/or fewer commands can be part of command stream 170 and/or more, different, and/or fewer data items can be provided as part of a command in command stream 170.

In scenario 300, operating session 1 is between crane operator 168 and crane 180 and operating session 2 is between truck operator 166*a* and truck 182*a*. Specification of one or more operator identifiers and one or more remotely-operable device identifiers can be determined from the operator(s) and remotely-operable device(s) associated with the session number. In other scenarios, operator identifier(s) and/or remotely-operable device identifiers can be specified directly as part of commands in command stream 170 and/or responses in response stream 186.

Security device 114 can be configured to be associated with a remotely-operable device. In some embodiments, security device 114 can be configured to generate additional signals based on input from the associated remotely-operable device and from reality rules related to the remotely-operable device stored in reality-rules database 334*a*. In particular embodiments, security device 114 can be configured to encode the additional signals into response stream 186 sent by or on behalf of the remotely-operable device. In other embodiments, security device 114 can be configured to decode command stream 170 to obtain additional signals from command stream 170 and convey the obtained additional signals to the associated remotely-operable device. In still other embodiments, security device 114 can be a component of the associated remotely-operable device.

Security device 114 can be configured to be associated with an operator and/or an operator device. In some embodiments, security device 114 can be configured to generate additional signals based on input from the associated operator and/or operator device and from reality rules related to the associated operator and/or the operator device stored in reality-rules database 334*a*. In particular embodiments, security device 114 can be configured to encode the additional signals into command stream 170 sent by or on behalf of the associated operator and/or operator device. In other embodiments, security device 114 can be configured to decode response stream 186 to obtain additional signals from command stream 170 and convey the obtained additional signals to the associated operator and/or operator device. In still other embodiments, security device 114 can be a component of the associated operator device.

FIG. 3 shows two example responses in response stream 186: responses 320 and 322. Response 320 to command 310 in operating session "1" includes a force feedback with a force "f3", related imagery provided on a video stream "vstr1" for session 1 ("sess1" as shown in FIG. 3), and related audio provided on an audio stream "astr3" for session 1, FIG. 3 also shows that the video stream "vstr1" of the related imagery also includes an additional signal "AS2" encoded within the video stream.

Response 322 to command 312 in operating session "2" includes a force feedback with a force "f4", related imagery as a file entitled "image237.jpg", and related audio provided on as a file "aud443.mp3". FIG. 3 also shows that the file "aud443.mp3" of the related audio also includes an encoded additional signal "AS3". Encoding additional signals within audio and video data is discussed in more detail in the context of at least FIG. 4. In other scenarios, more, different and/or fewer responses can be part of response stream 186 and/or more, different, and/or fewer data items can be provided as part of a response in response stream 186.

In scenario 300, each of command stream 170 and response stream 186 conveys additional signals, such as discussed above in the context of at least FIG. 1A. In some embodiments, security device 114 can be configured to encode additional signals into command stream 170 and/or response stream 186 and/or decode additional signals from command stream 170 and/or response stream 186, such as, but not limited to additional signals AS1*a*, AS1*b*, AS2, and AS3.

In scenario 300, commands from command stream 170 and responses from response stream 186 can be provided as inputs to security device 114. Security device 114 can include secure coprocessor 330 to provide processor(s) (e.g., central processing units (CPUs), graphics processing units (GPUs), math coprocessors, etc.), security-specific hardware (e.g., application-specific integrated circuits (ASICs), other circuits including other integrated circuits), memory, interconnection devices (e.g., buses), firmware, and/or software for security-related processing.

Examples of security-related processing include, but are not limited to, signature generator 332 and encryption/decryption device 336, Signature generator 332 can determine or generate a signature for an operator of a remotely-operable device based on commands input from command stream 170, responses input from response stream 186, and/or other inputs (e.g., timing data, remotely-operable device schedules, etc.). Signature generation is described in more detail in at least FIG. 3 below.

Signatures and associated identities (IDs) can be stored in signature/ID database 334. For example, signature/ID database 334 can receive a query with a given ID, retrieve a stored signature associated with the given ID, and provide a query response with the given ID. As another example, signature/ID database 334 can receive another query with a given signature, retrieve a stored ID associated with the given signature, and provide a query response with the stored ID. If, in after receiving a particular query for an ID or signature, no matching signature or ID, the query response can indicate that no matching data is available. In some scenarios, signature/ID database 334 can receive other queries, retrieve other data based on the other queries, and provide query reports based on the retrieved other data.

In combination, signature generator 332 can generate a signature from commands, response, and other inputs as discussed immediately above, form a query with the generated signature to signature/ID database 334, and receive a query response from signature/ID database 334 with an ID associated with the generated signature.

Then, security device 114 can generate reports and/or take action(s) based on the information in command stream 170 and response stream 186 as well as signature information, such as, but not limited to, ID reports (IDRs), anomaly reports (ARs), security reports (SRs), security anomalies (SAs), and action reports (Acts) as shown in FIG. 3.

ID reports and anomaly reports can be based on signature information. Example ID report 340, as shown in FIG. 3, indicates that a signature of "Operator 73" has been generated and matched with an ID for operating remotely-operable device "Crane 180". Example anomaly report 350, shown in FIG. 3, indicates that a signature has been generated for remotely-operable device "Crane 180" that does not match the signature of "Operator 168", and so anomaly report 350 indicates that operator 73 is no longer associated with crane 180.

Security reports and security anomalies can based on additional signals conveyed with command stream 170 and/or response stream 186. Example security report 342, shown in FIG. 3, indicates that no security issues have been detected regarding "Session 2" for the last 10 minutes. Such periodic reports can indicate that additional signals are being processed successfully and so indicate that command stream 170 and/or response stream 186 are likely not be subject to attack. Security report 344 indicates that "Security Data"; e.g., some or all additional signals, are "Missing" regarding message (msg) "12" of "Session 1", indicating a possible attack, as expected additional signals were not received. Example anomaly report 350, shown in FIG. 3, indicates that a signature has been generated for remotely-operable device "Crane 180" that does not match the signature of "Operator 168", and so anomaly report 350 indicates that operator 73 is no longer associated with crane 180.

Example actions that can be taken include, but are not limited to, instructing a remotely-operable device to use a backup command, instructing a remotely-operable device to reach a safe stop position, instructing a remotely-operable device to enter or exit a mode of operation, inhibiting transmission of one or more commands from one or more operator devices and/or to one or more specified remotely-operable devices, enabling transmission of one or more commands from one or more operator devices and/or to the one or more specified remotely-operable devices, inhibiting transmission of one or more responses from one or more specified remotely-operable devices and/or to one or more operator devices, enabling transmission of one or more responses from one or more specified remotely-operable devices and/or to one or more operator devices, requesting additional information about an operator (e.g., request the operator generate a command with a name, personal ID number (PIN), biometric information, etc.), request retransmission of commands and/or responses, send command(s) to start or stop one or more specified remotely-operable devices, and send command(s) to start or stop one or more specified operator devices. In some cases, action reports can include information about actions taken by a remotely-operable device other than actions taken in response to an unencoded command in command stream 170; e.g., actions to reach a safe stop position, use of backup instructions, actions taken while in a (semi)autonomous mode, and other actions taken by the remotely-operable device.

FIG. 3 shows three example action reports action report 360 for "Mov[ing] Actuator D of Crane 182 to position X" and "stop[ping] Actuator D" as actions taken to reach a safe stop position for crane 182, action report 362 where "Truck 182a" was "Slow[ed]" to "10 MPH" while in a (semi) autonomous mode "SAM", and action report 364 indicating a "Backup instruction [was] used". Many other reports and actions are possible as well.

Example Message Layouts for Encoded Messages

Figure 4:
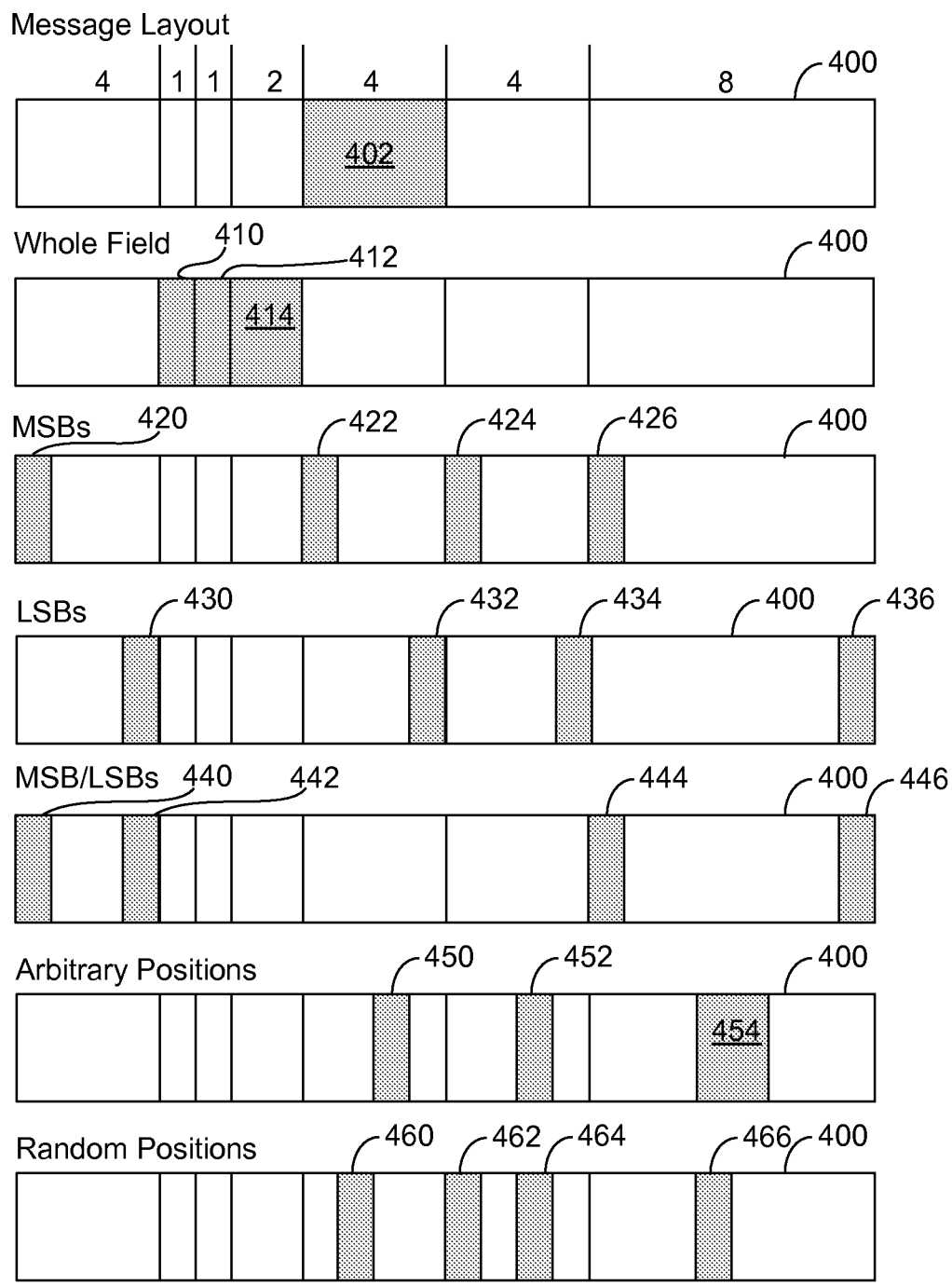
FIG. 4 depicts example message layouts, in accordance with an embodiment.

FIG. 4 depicts example layouts of part or all of message 400, in accordance with an embodiment. Message 400 can be a command message; e.g., part of a command message stream, a feedback message, e.g., part of a feedback message stream, or some other type of message. FIG. 4A shows a top layout of message 400 labeled "Message Layout" with seven fields. The seven fields are shown, from left to right, being respectively configured to store four, one, one, two, four, four, and eight units of data for message 400 for a total of 24 units of data. Units of data can be bits, bytes, or some other unit of data storage.

Field 402 is shown in FIG. 4 using a grey color to indicate that the four units of data for field 402 are intended to be encoded units of data; e.g., configured for carrying the additional signals discussed above in the context of FIGS. 1A through 3. The top layout of FIG. 4 also shows the six fields other than field 402 using a white color to indicate that the 20 units of data for the six fields of data are intended to be unencoded. Each of the seven layouts shown in FIG. 4 are configured with the same seven fields shown in the "Message Layout" (top) layout of FIG. 4, and so are configured to hold four units of encoded data and 20 units of unencoded data, for a total of 24 units of data.

The "Whole Field" layout, shown second from top in FIG. 4, shows that three entire, or whole, fields 410, 412, 414 are used to encode data for message 400. The unencoded data that would otherwise be stored in fields 410, 412, and 414 can be stored in the otherwise unused fifth field from the right (corresponding to field 402) in the Whole Field layout. As such, message 400 using the Whole Field layout, and the other layouts in shown in FIG. 4, can include four units of encoded data (depicted in FIG. 4 using grey) and 20 units of unencoded data (depicted in FIG. 4 using white).

In some protocols, most-significant bits (MSBs) and/or least-significant bits (LSBs) of fields are reserved, designated for expansion, or otherwise indicated as rarely or never used. As such, MSBs and/or LSBs of fields of data can be used to encode additional signals, such as shown in respective layouts labeled "MSBs" (third layout from top) and "LSBs" (fourth layout from top) in FIG. 4. Combinations of MSBs and LSBs can be used as well, such as shown in the layout labeled "MSB/LSBs" (fifth layout from top) in FIG. 4. Further, data can be encoded in arbitrary or random positions of message 400 in FIG. 4, such as shown in layouts respectively labeled "Arbitrary Positions" (sixth layout from top) and "Random Positions" (seventh layout from top). The unencoded data that would otherwise be stored in fields of these layouts can be stored in the otherwise unused units of data in the fifth field from the right in the respective layout (corresponding to field 402 in the top layout of FIG. 4), as the fifth field is originally designated for storing encoded data.

The layouts depicted in FIG. 4 and other layouts can be varied to enable changing locations of encoded data around between messages, and so increase the difficulty of determining the presence of encoded data in a message stream including several copies of message 400.

In examples not shown in FIG. 4, other types of data can be encoded to convey additional signals, such as, but not limited to audio, video, binary and/or other types of data that are conveyed in command, feedback, and/or other messages. For example, steganographic techniques can be used to encode additional signals into image and/or video data, and similar techniques to steganography can be used to encode additional signals into binary data. As another example, modulation of pre-determined frequencies and/or addition of data carried on pre-determined frequencies of audio data can be used to encode additional signals into audio data. Many other examples of encoding additional signals into data into command, feedback, and/or other messages.

An Example Computing Network

Figure 5A:
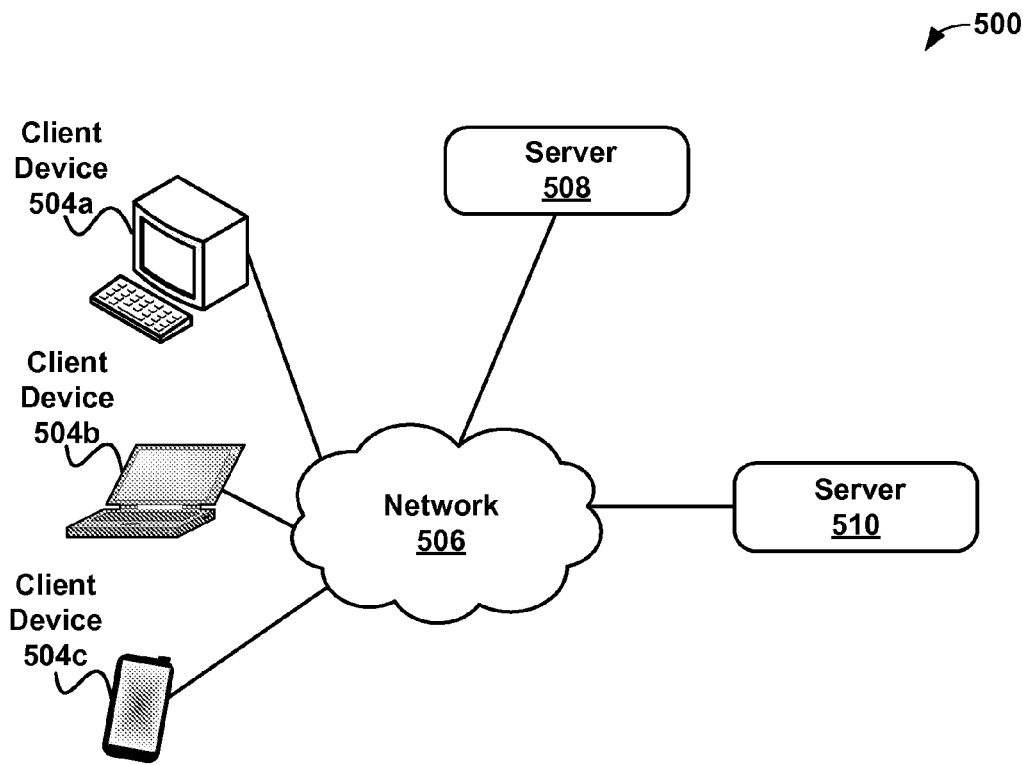
FIG. 5A is a block diagram of an example computing network, in accordance with an embodiment.

FIG. 5A is a block diagram of example computing network 500 in accordance with an example embodiment. In FIG. 5A, servers 508 and 510 are configured to communicate, via a network 506, with client devices 504a, 504b, and 504c. As shown in FIG. 5A, client devices can include a personal computer 504a, a laptop computer 504b, and a smart-phone 504c. More generally, client devices 504a-504c (or any additional client devices) can be any sort of computing device, such as a workstation, network terminal, desktop computer, laptop computer, wireless communication device (e.g., a cell phone or smart phone), and so on.

The network 506 can correspond to a local area network, a wide area network, a corporate intranet, the public Internet, combinations thereof, or any other type of network(s) configured to provide communication between networked computing devices. In some embodiments, part or all of the communication between networked computing devices can be secured.

For example, network 116 and/or secure network 172 can be embodiments of network 506. As such, network 506 can be used to connect remotely-operable devices in one or more remote environments with operator devices in one or more operator environments, such as, but not limited to, the remote environments and operator environments shown in FIGS. 1A-1D.

Servers 508 and 510 can share content and/or provide content to client devices 504a-504c. As shown in FIG. 5A, servers 508 and 510 are not physically at the same location. Alternatively, recipe servers 508 and 510 can be co-located, and/or can be accessible via a network separate from network 506. Although FIG. 5A shows three client devices and two servers, network 506 can service more or fewer than three client devices and/or more or fewer than two servers.

An Example Computing Device

Figure 5B:
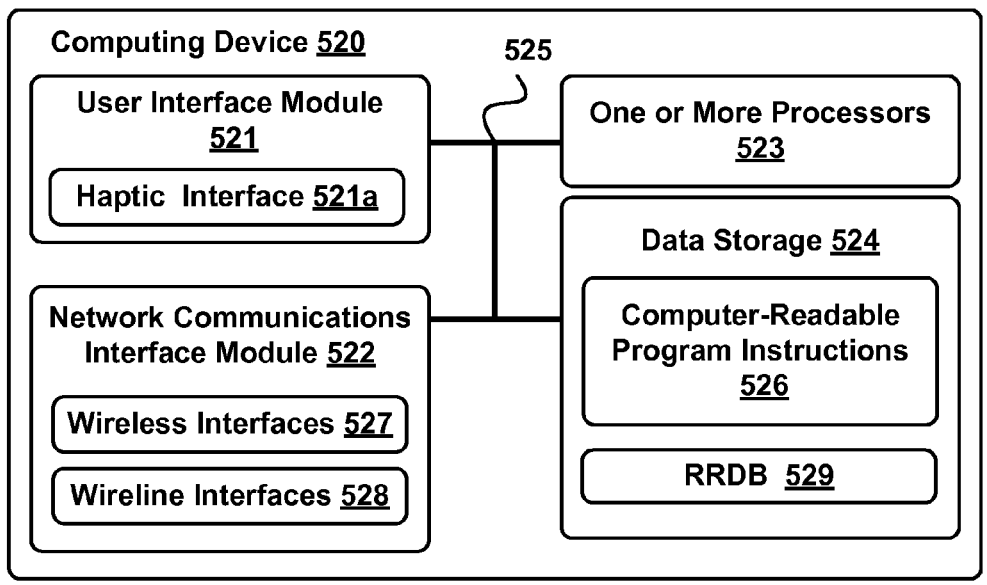
FIG. 5B is a block diagram of an example computing device, in accordance with an embodiment.

FIG. 5B is a block diagram of an example computing device 520 including user interface module 521, network-communication interface module 522, one or more processors 523, and data storage 524, in accordance with embodiments of the invention.

In particular, computing device 520 shown in FIG. 5A can be configured to perform one or more functions of client devices 504a-504c, network 506, and/or servers 508, 510. Computing device 520 may include a user interface module 521, a network-communication interface module 522, one or more processors 523, and data storage 524, all of which may be linked together via a system bus, network, or other connection mechanism 525.

Computing device 520 can be a desktop computer, laptop or notebook computer, personal data assistant (PDA), mobile phone, embedded processor, or any similar device that is equipped with at least one processing unit capable of executing machine-language instructions that implement at least part of the herein-described techniques and methods, including but not limited to methods 600 and 650 described below with respect to FIGS. 6A and 6B.

User interface 521 can receive input and/or provide output, perhaps to a user. User interface 521 can be configured to send and/or receive data to and/or from user input from input device(s), such as a keyboard, a keypad, a touch screen, a computer mouse, a track ball, a joystick, and/or other similar devices configured to receive input from a user of the computing device 520. User interface 521 can be configured to provide output to output display devices, such as one or more cathode ray tubes (CRTs), liquid crystal displays (LCDs), light emitting diodes (LEDs), displays using digital light processing (DLP) technology, printers, light bulbs, and/or other similar devices capable of displaying graphical, textual, and/or numerical information to a user of computing device 520. User interface module 521 can also be configured to generate audible output(s), such as a speaker, speaker jack, audio output port, audio output device, earphones, and/or other similar devices configured to convey sound and/or audible information to a user of computing device 520. As shown in FIG. 5B, user interface can be configured with haptic interface 521a that can receive inputs related to a Haptic Interface Point, a remote device configured to be controlled by haptic interface 521a, and/or other inputs, and provide haptic outputs such as tactile feedback, vibrations, forces, motions, and/or other touch-related outputs.

Network-communication interface module 522 can be configured to send and receive data over wireless interfaces 527 and/or wired interfaces 528 via a network, such as network 506. Wired interface(s) 528, if present, can comprise a wire, cable, fiber-optic link and/or similar physical connection to a data network, such as a wide area network (WAN), a local area network (LAN), one or more public data networks, such as the Internet, one or more private data networks, or any combination of such networks. Wireless interface(s) 527 if present, can utilize an air interface, such as a ZigBee, Wi-Fi, and/or WiMAX interface to a data network, such as a WAN, a LAN, one or more public data networks (e.g., the Internet), one or more private data networks, or any combination of public and private data networks.

In some embodiments, network-communication interface module 522 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encrypted) and/or decrypted using one or more cryptographic protocols and/or algorithms, such as, but not limited to, DES, AES, RSA, Diffie-Hellman, and/or DSA. Other cryptographic protocols and/or algorithms can be used as well as or in addition to those listed herein to secure (and then decrypt) communications.

Processor(s) 523 can include one or more central processing units, computer processors, mobile processors, digital signal processors (DSPs), microprocessors, computer chips, and/or other processing units configured to execute machine-language instructions and process data. Processor(s) 523 can be configured to execute computer-readable program instructions 526 that are contained in data storage 524 and/or other instructions as described herein.

Data storage 524 can include one or more physical and/or non-transitory storage devices, such as read-only memory (ROM), random access memory (RAM), removable-disk-drive memory, hard-disk memory, magnetic-tape memory, flash memory, and/or other storage devices. Data storage 524 can include one or more physical and/or non-transitory storage devices with at least enough combined storage capacity to contain computer-readable program instructions 526 and any associated/related data structures.

In particular, data storage 524 cart be configured to store reality-rules data base 529, which in turn can be configured to store one or more reality rules. The reality rules can include constraints on computing device 520 in certain embodiments and scenarios; i.e., where computing device 520 is configured as part or all of a remotely-operable device. Reality-rules data bases, such as reality-rules data base 529, are discussed above in the context of at least FIGS. 1A through 3.

Computer-readable program instructions 526 and any data structures contained in data storage 526 include computer-readable program instructions executable by processor(s) 523 and any storage required, respectively, to perform at least pail of herein-described methods, including but not limited to methods 600 and 650 described below with respect to FIGS. 6A and 6B.

Example Methods of Operation

Figure 6A:
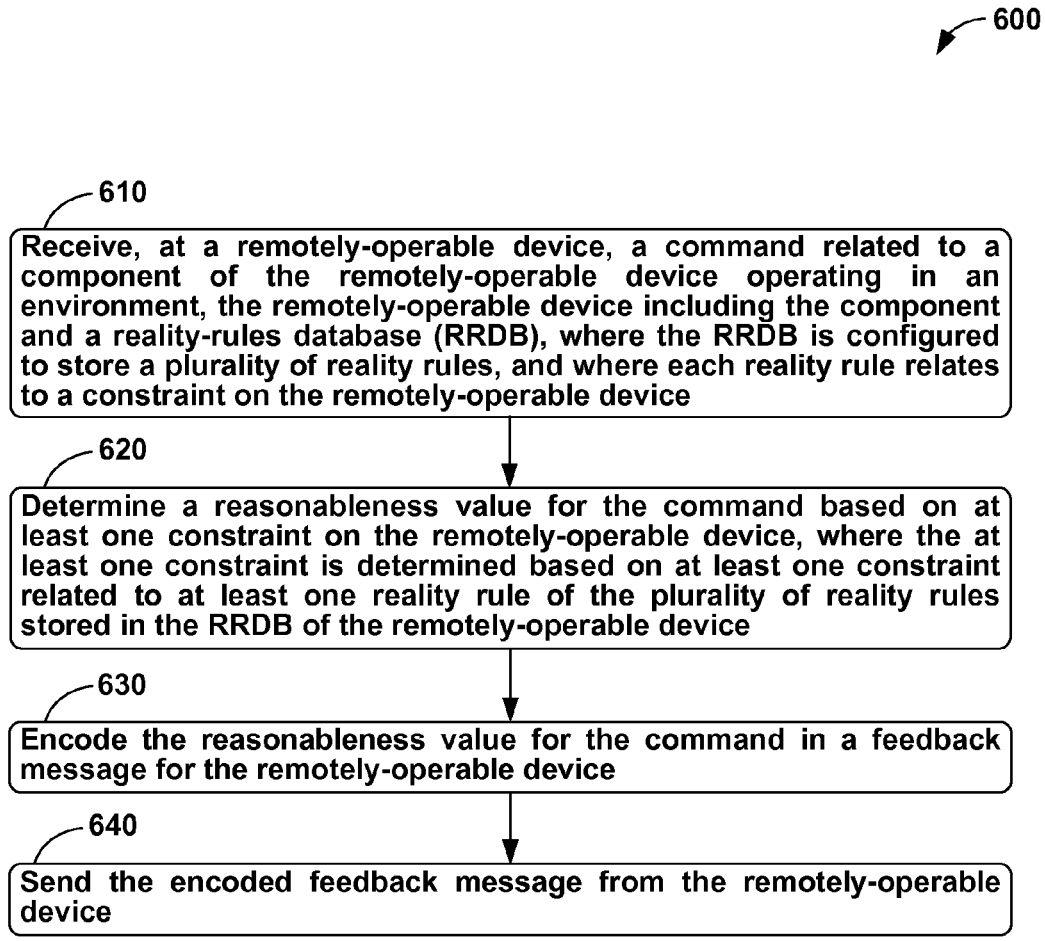
FIG. 6A is a flow chart of an example method, in accordance with an embodiment.

FIG. 6A is a flow chart of an example method 600. Method 600 can be carried out by a remotely-operable device, such as discussed above in the context of at least FIGS. 1A-5B.

Method 600 can begin at block 610, where a remotely-operable device can receive a command related to a component of the remotely-operable device operating in an environment, such as discussed above at least in the context of FIGS. 1A through 3. The remotely-operable device can include the component and a RRDB, such as discussed above at least in the context of FIGS. 1A through 3. The RRDB can be configured to store a plurality of reality rules, where each reality rule can relates to a constraint on the remotely-operable device, such as discussed above at least in the context of FIGS. 1A through 3.

In some embodiments, the plurality of reality rules can include at least one rule selected from the group of rules consisting of: a rule about a range of motion of the component, a range of motion of the remotely-operable device, a rule about maximum velocity of the component, a rule about a maximum velocity of the remotely-operable device, a rule about a maximum acceleration of the component, a rule about a maximum acceleration of the remotely-operable device, a rule about a location for operating the remotely-operable device, a rule about a location for not operating the remotely-operable device, a rule about a stress on the component, a rule about a stress on the remotely-operable device, a rule about a distance between the component and another component of the remotely-operable device, and a rule about a minimum distance between the remotely-operable device and another device.

At block 620, the remotely-operable device can determine a reasonableness value for the command based on at least one constraint on the remotely-operable device, such as discussed above at least in the context of FIGS. 1A through 3. At least one constraint can be determined based on at least one constraint related to at least one reality rule of the plurality of reality rules stored in the RRDB of the remotely-operable device, such as discussed above at least in the context of FIGS. 1A through 3.

In some embodiments, such as discussed above at least in the context of FIG. 3, determining a reasonableness value for the command can include: determining a current status of the component of the remotely-operable device; determining a possible-future status of the component based on the current status, wherein the possible-future status indicates a status in the event the command were executed; providing a query to the RRDB related to the component; in response to the query, receiving data regarding at least one constraint; and determining the reasonableness value based on the future status and the data regarding at least one constraint.

At block 630, the remotely-operable device can encode the reasonableness value for the command in a feedback message, such as discussed above at least in the context of FIGS. 1A through 4.

In some embodiments, such as discussed above at least in the context of FIG. 4, the feedback message can include a plurality of fields. Then, encoding the reasonableness value for the command can include encoding at least one field of the plurality of fields of the feedback message with the reasonableness value. In particular of these embodiments, such as discussed above at least in the context of FIG. 4, the reasonableness value for the command can include one or more bits. Then, encoding the reasonableness value for the command can include encoding at least one field of the plurality of fields with at least one bit of the one or more bits of the reasonableness value.

In other of these embodiments, the feedback message can include an image. Then, encoding the reasonableness value for the command can include encoding the image with the reasonableness value. In particular of these embodiments, the reasonableness value for the command can include one or more bits. Then, encoding the image with the reasonableness value can include encoding the image with the one or more bits of the reasonableness value using a steganographic technique.

At block 640, the remotely-operable device can send the encoded feedback message, such as discussed above at least in the context of FIGS. 1A through 3.

In some embodiments, such as discussed above at least in the context of FIG. 3, method 600 can also include: determining whether the reasonableness value exceeds a threshold reasonableness value; and after determining that the reasonableness value exceeds the threshold reasonableness value, at least partially executing the command at the remotely-operable device.

In some embodiments, such as discussed above at least in the context of FIG. 3, the command can include a backup command. In particular of these embodiments, method 600 can also include: determining whether the reasonableness value exceeds a threshold reasonableness value; and after determining that the reasonableness value does not exceed the threshold reasonableness value, determining that the command is not feasible for at least partial execution.

In more particular of these embodiments, method 600 can also include: after determining that the command is not feasible for at least partial execution, determining whether the backup command is feasible for at least partial execution; and after determining that the backup command is feasible for at least partial execution, at least partially executing the backup command. In even more particular of these embodiments, method 600 can also include: after determining that the backup command is not feasible for at least partial execution, performing a default operation for the remotely-operable device; and sending information indicating that the default operation has been performed from the remotely-operable device.

Figure 6B:
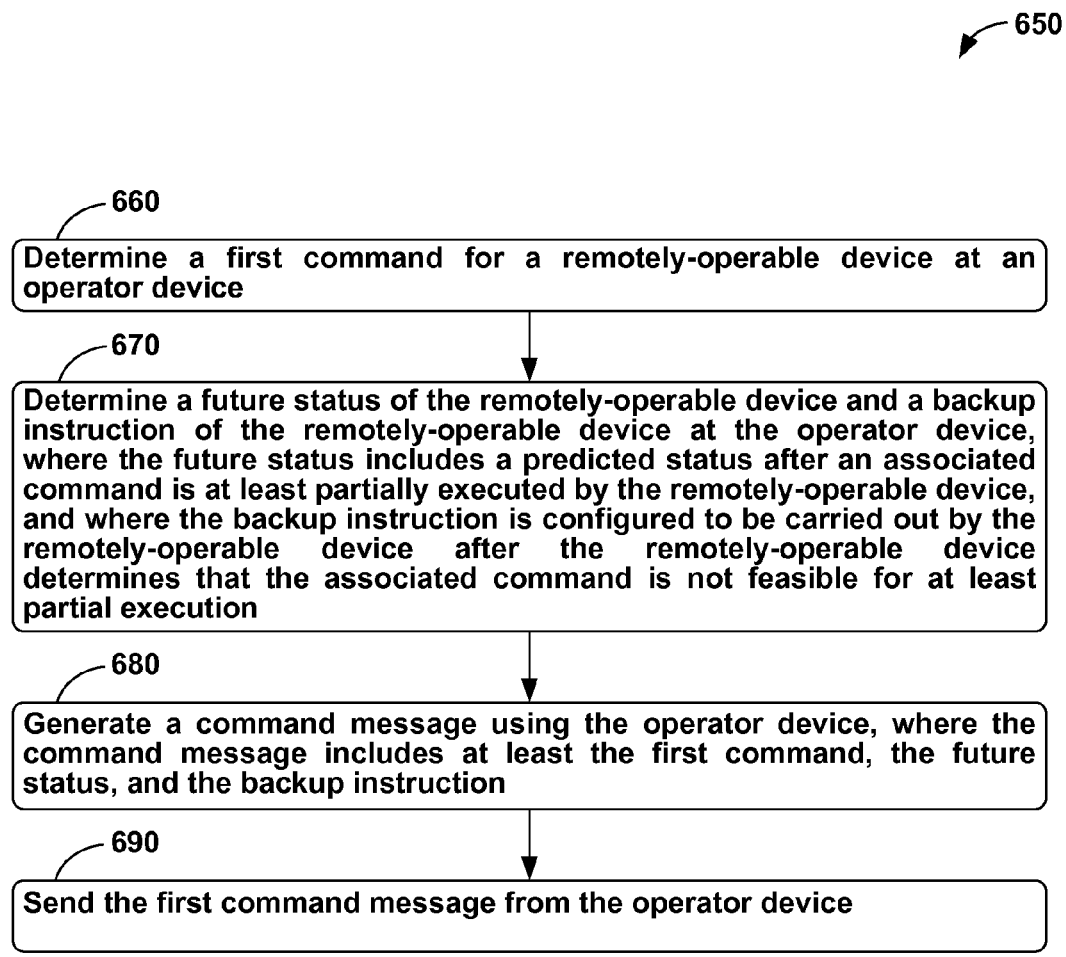
FIG. 6B is a flow chart of another example method, in accordance with an embodiment.

FIG. 6B is a flow chart of an example method 650. Method 650 can be carried out by an operator device, such as discussed above in the context of at least FIGS. 1A-5B.

Method 650 can begin at block 660. At block 660, an operator device can determine a first command for a remotely-operable device, such as discussed above in the context of at least FIGS. 1A through 3.

At block 670, the operator device can determine a future status and a backup command of the remotely-operable device, such as discussed above in the context of at least FIGS. 1A through 3. The future status can include a predicted status of the remotely-operable device after an associated command is at least partially executed by the remotely-operable device. The backup command is configured to be carried out by the remotely-operable device after the remotely-operable device determines that the associated command is not feasible for at least partial execution.

In some embodiments, the associated command can be the first command. In other embodiments, the associated command can be a command other than the first command. In particular of these embodiments, the associated command can be a command sent to the prior to the first command.

At block 680, the operator device can generate a command message that includes at least the first command, the future status, and the backup command, such as discussed above in the context of at least FIGS. 1A through 3. In some embodiments, the command message can include a plurality of fields with each field including one or more bits. Also, the future status can be configured to be encoded in a first set of bits. Then, generating the command message can include encoding at least the first set of bits into one or more bits of at least one field of the plurality of fields. In other embodiments, the command message can include a plurality of fields with each field including one or more bits. Also, the backup command can be configured to be encoded as a second set of bits. Then, generating the command message can include encoding at least the second set of bits into one or more bits of at least one field of the plurality of fields.

At block 690, the operator device can send the command message, such as discussed above in the context of at least FIGS. 1A through 3. In some embodiments, method 650 can also include receiving a report that a default operation of the remotely-operable device has been performed, where the default operation differs from both the first command and the associated command.

CONCLUSION

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

The above description provides specific details for a thorough understanding of and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

Numerous modifications and variations of the present disclosure are possible in light of the above teachings.

What is claimed:

1. A method, comprising:
receiving, at a remotely-operable device, a command related to a component of the remotely-operable device operating in an environment, the remotely-operable device comprising the component and a reality-rules database (RRDB), wherein the RRDB is configured to store a plurality of reality rules, and wherein each reality rule relates to a constraint on the remotely-operable device;
determining a first value for the command based on at least one constraint on at least the component of the remotely-operable device while operating in the environment, wherein the at least one constraint is determined based on at least one reality rule of the plurality of reality rules stored in the RRDB of the remotely-operable device, and wherein determining the first value for the command comprises:
determining a current status of the component of the remotely-operable device,
determining a possible-future status of the component based on the current status, wherein the possible-future status indicates a status in the event the command was executed,
providing a query to the RRDB related to the component,
in response to the query, receiving data regarding the at least one constraint on the remotely-operable device, and
determining the first value based on the possible-future status and the data regarding the at least one constraint on the remotely-operable device;
encoding the first value for the command in a feedback message for the remotely-operable device; and
sending the encoded feedback message from the remotely-operable device.

2. The method of claim 1, wherein the plurality of reality rules comprise a plurality of reality rules applicable to the command, and wherein determining the first value for the command comprises:
determining the first value based on the plurality of reality rules applicable to the command.

3. The method of claim 1, further comprising:
determining whether the first value exceeds a threshold value; and
after determining that the first value exceeds the threshold value, at least partially executing the command at the remotely-operable device.

4. The method of claim 1, wherein the command comprises a backup command.

5. The method of claim 4, further comprising:
determining whether the first value exceeds a threshold value; and after determining that the first value does not exceed the threshold value, determining that the command is not feasible for at least partial execution.

6. The method of claim 5, further comprising:

after determining that the command is not feasible for at least partial execution, determining whether the backup command is feasible for at least partial execution; and after determining that the backup command is feasible for at least partial execution, at least partially executing the backup command.

7. The method of claim 6, further comprising:

after determining that the backup command is not feasible for at least partial execution, performing a default operation for the remotely-operable device; and sending information indicating that the default operation has been performed from the remotely-operable device.

8. The method of claim 1, wherein the feedback message comprises a plurality of fields, and wherein encoding the first value for the command comprises encoding at least one field of the plurality of fields of the feedback message with the first value.

9. The method of claim 8, wherein the first value for the command comprises one or more bits, and wherein encoding the first value for the command comprises encoding at least one field of the plurality of fields with at least one bit of the one or more bits of the first value.

10. The method of claim 1, wherein the feedback message comprises an image, and wherein encoding the first value for the command comprises encoding the image with the first value.

11. The method of claim 10, wherein the first value for the command comprises one or more bits, and wherein encoding the image with the first value comprises encoding the image with the one or more bits of the first value using a steganographic technique.

12. The method of claim 1, wherein the plurality of reality rules comprise at least one rule selected from the group of rules consisting of: a rule about a range of motion of the component, a range of motion of the remotely-operable device, a rule about maximum velocity of the component, a rule about a maximum velocity of the remotely-operable device, a rule about a maximum acceleration of the component, a rule about a maximum acceleration of the remotely-operable device, a rule about a location for operating the remotely-operable device, a rule about a location for not operating the remotely-operable device, a rule about a stress on the component, a rule about a stress on the remotely-operable device, a rule about a distance between the component and another component of the remotely-operable device, and a rule about a minimum distance between the remotely-operable device and another device.

13. A remotely-operable device, comprising:

a component;

a processor; and a non-transitory tangible computer readable medium configured to store at least a reality-rules database (RRDB) and executable instructions, wherein the RRDB is configured to store a plurality of reality rules, wherein each reality rule relates to a constraint on the remotely-operable device, and wherein the executable instructions, when executed by the processor, cause the remotely-operable device to perform functions comprising:

receiving a command related to the component operating in an environment;

determining a first value for the command based on at least one constraint on at least a portion of the remotely-operable device while operating in the environment, wherein the at least one constraint is determined based on at least one constraint related to at least one reality rule of the plurality of reality rules stored in the RRDB, and wherein determining the first value for the command comprises:

determining a current status of the component of the remotely-operable device, determining a possible-future status of the component based on the current status, wherein the possible-future status indicates a status in the event the command was executed, providing a query to the RRDB related to the component, in response to the query, receiving data regarding the at least one constraint on the remotely-operable device, and determining the first value based on the possible-future status and the data regarding the at least one constraint on the remotely-operable device;

encoding the first value for the command in a feedback message; and sending the encoded feedback message.

14. The remotely-operable device of claim 13, wherein the functions further comprise:

determining whether the first value exceeds a threshold value; and after determining that the first value exceeds the threshold value, at least partially executing the command at the remotely-operable device.

15. The remotely-operable device of claim 13, wherein the command comprises a backup command.

16. The remotely-operable device of claim 15, wherein the functions further comprise:

determining whether the first value exceeds a threshold value; and after determining that the first value does not exceed the threshold value, determining that the command is not feasible for at least partial execution.

17. The remotely-operable device of claim 16, wherein the functions further comprise:

after determining that the command is not feasible for at least partial execution, determining whether the backup command is feasible for at least partial execution; and after determining that the backup command is feasible for at least partial execution, at least partially executing the backup command.

18. The remotely-operable device of claim 17, wherein the functions further comprise:

after determining that the backup command is not feasible for at least partial execution, performing a default operation for the remotely-operable device; and sending information indicating that the default operation has been performed from the remotely-operable device.

19. The remotely-operable device of claim 13, wherein the plurality of reality rules comprise at least one rule selected from the group of rules consisting of: a rule about a range of motion of the component, a range of motion of the remotely-operable device, a rule about maximum velocity of the component, a rule about a maximum velocity of the remotely-operable device, a rule about a maximum acceleration of the component, a rule about a maximum acceleration of the remotely-operable device, a rule about a location for operating the remotely-operable device, a rule about a location for not operating the remotely-operable device, a rule about a stress on the component, a rule about a stress on the remotely-operable device, a rule about a distance between the component and another component of the remotely-operable device, and a rule about a minimum distance between the remotely-operable device and another device.

20. A non-transitory tangible computer readable medium configured to store at least executable instructions that, when executed by a processor of a remotely-operable device, cause the remotely-operable device to perform functions comprising:
receiving a command related to a component of the remotely-operable device operating in an environment;
determining a first value for the command based on at least one constraint on at least the component of the remotely-operable device while operating in the environment, wherein the at least one constraint is determined based on at least one constraint related to at least one reality rule of a plurality of reality rules stored in a reality-rules data base (RRDB), and wherein determining the first value for the command comprises:
determining a current status of the component of the remotely-operable device,
determining a possible-future status of the component based on the current status, wherein the possible-future status indicates a status in the event the command was executed,
providing a query to the RRDB related to the component,
in response to the query, receiving data regarding the at least one constraint on the remotely-operable device, and
determining the first value based on the possible-future status and the data regarding the at least one constraint on the remotely-operable device;
encoding the first value for the command in a feedback message; and
sending the encoded feedback message.

21. A method, comprising:
receiving, at a remotely-operable device, a command related to a component of the remotely-operable device operating in an environment, the remotely-operable device comprising the component and a reality-rules database (RRDB), wherein the RRDB is configured to store a plurality of reality rules, and wherein each reality rule relates to a constraint on the remotely-operable device, wherein the plurality of reality rules comprise at least one rule selected from the group of rules consisting of: a rule about a range of motion of the component, a range of motion of the remotely-operable device, a rule about maximum velocity of the component, a rule about a maximum velocity of the remotely-operable device, a rule about a maximum acceleration of the component, a rule about a maximum acceleration of the remotely-operable device, a rule about a location for operating the remotely-operable device, a rule about a location for not operating the remotely-operable device, a rule about a stress on the component, a rule about a stress on the remotely-operable device, a rule about a distance between the component and another component of the remotely-operable device, and a rule about a minimum distance between the remotely-operable device and another device;
determining a first value for the command based on at least one constraint on at least the component of the remotely-operable device while operating in the environment, wherein the at least one constraint is determined based on at least one reality rule of the plurality of reality rules stored in the RRDB of the remotely-operable device;
encoding the first value for the command in a feedback message for the remotely-operable device; and
sending the encoded feedback message from the remotely-operable device.

* * * * *